(12) United States Patent
Hotta et al.

(10) Patent No.: US 12,031,130 B2
(45) Date of Patent: Jul. 9, 2024

(54) COMPOSITION FOR MODIFYING TARGET GENE

(71) Applicant: TAKEDA PHARMACEUTICAL COMPANY LIMITED, Osaka (JP)

(72) Inventors: Akitsu Hotta, Kyoto (JP); Masataka Ifuku, Kyoto (JP); Naoko Fujimoto, Kyoto (JP); Kumiko Iwabuchi, Kyoto (JP); Eriya Kenjo, Kanagawa (JP); Yukimasa Makita, Kanagawa (JP); Rumiko Ochiai, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 426 days.

(21) Appl. No.: 16/958,006

(22) PCT Filed: Dec. 27, 2018

(86) PCT No.: PCT/JP2018/048034
§ 371 (c)(1),
(2) Date: Jun. 25, 2020

(87) PCT Pub. No.: WO2019/131829
PCT Pub. Date: Jul. 4, 2019

(65) Prior Publication Data
US 2021/0371854 A1 Dec. 2, 2021

(30) Foreign Application Priority Data
Dec. 28, 2017 (JP) ................. 2017-254798

(51) Int. Cl.
*C12N 15/11* (2006.01)
*A01K 67/027* (2006.01)
*A61K 47/24* (2006.01)
*C12N 9/22* (2006.01)

(52) U.S. Cl.
CPC ............ *C12N 15/11* (2013.01); *A01K 67/027* (2013.01); *A61K 47/24* (2013.01); *C12N 9/22* (2013.01); *A01K 2217/00* (2013.01); *A01K 2227/10* (2013.01); *C12N 2310/20* (2017.05); *C12N 2320/30* (2013.01)

(58) Field of Classification Search
CPC ...... C12N 15/11; C12N 9/22; C12N 2310/20; C12N 2320/30; C12N 15/102; C12N 15/907; A01K 2217/00; A01K 2227/10; A61K 31/7105; A61K 9/0019; A61K 9/5123; A61K 31/7088; A61K 48/00; C07K 14/4708
See application file for complete search history.

(56) References Cited

U.S. PATENT DOCUMENTS

| 7,745,651 | B2 | 6/2010 | Heyes et al. |
| 7,982,027 | B2 | 7/2011 | MacLachlan et al. |
| 8,969,543 | B2 | 3/2015 | Jeong et al. |
| 9,371,271 | B2 | 6/2016 | Kubo et al. |
| 2003/0124727 | A1 | 7/2003 | Gaucheron et al. |
| 2004/0043952 | A1 | 3/2004 | Niedzinski et al. |
| 2012/0276209 | A1 | 11/2012 | Cullis et al. |
| 2015/0232883 | A1 | 8/2015 | Dahlman et al. |

(Continued)

FOREIGN PATENT DOCUMENTS

| CN | 104116643 A | 10/2014 |
| CN | 104873976 A | 9/2015 |

(Continued)

OTHER PUBLICATIONS

Young et al. A Single CRISPR-Cas9 Deletion Strategy that Targets the Majority of DMD Patients Restores Dystrophin Function in hiPSC-Derived Muscle Cells. Cell Stem Cell (2016), 18:533-540. (Year: 2016).*

(Continued)

*Primary Examiner* — Iqbal H Chowdhury
(74) *Attorney, Agent, or Firm* — McCarter & English, LLP; David G. Conlin

(57) ABSTRACT

The present invention provides a delivery technique for delivering a gene modification tool capable of providing a high gene modification efficiency in cells. The composition according to the present invention is a composition for inducing gene modification at a target gene locus in a cell, the composition containing 1) a compound represented by formula (I) or a salt thereof; 2) a structural lipid; and 3) a guide RNA or a DNA including a sequence encoding the guide RNA, and/or an RNA-guided nuclease or a nucleic acid including a sequence encoding the RNA-guided nuclease. In formula (I), n represents an integer of 2 to 5, R represents a linear $C_{1-5}$ alkyl group, a linear $C_{7-11}$ alkenyl group, or a linear $C_{11}$ alkadienyl group, and wavy lines each independently represent a cis-type bond or a trans-type bond.

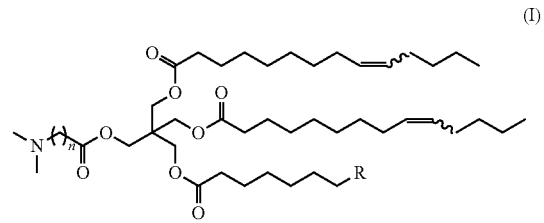

(I)

27 Claims, 6 Drawing Sheets
Specification includes a Sequence Listing.

(56) References Cited

U.S. PATENT DOCUMENTS

| | | |
|---|---|---|
| 2015/0343062 A1 | 12/2015 | Kuboyama et al. |
| 2017/0015994 A1 | 1/2017 | Anderson et al. |
| 2017/0197903 A1 | 7/2017 | Hoashi |
| 2018/0353434 A1 | 12/2018 | Hatanaka et al. |
| 2021/0052646 A1 | 2/2021 | Kuwae et al. |

FOREIGN PATENT DOCUMENTS

| | | |
|---|---|---|
| CN | 106536729 A | 3/2017 |
| CN | 106573877 A | 4/2017 |
| CN | 107427531 A | 12/2017 |
| CN | 111542338 A | 8/2020 |
| EP | 2611419 A2 | 7/2013 |
| EP | 3093283 A1 | 11/2016 |
| EP | 3178807 B1 | 4/2020 |
| EP | 3733211 A1 | 11/2020 |
| RU | 2573409 C2 | 1/2016 |
| WO | 2003102150 A2 | 12/2003 |
| WO | 2012/028524 A2 | 3/2012 |
| WO | 2014197748 A2 | 12/2014 |
| WO | 2016021683 A1 | 2/2016 |
| WO | 2016025469 A1 | 2/2016 |
| WO | 2016/153012 A1 | 9/2016 |
| WO | 2016197133 A1 | 12/2016 |
| WO | 2017072590 A1 | 5/2017 |

OTHER PUBLICATIONS

Wei et al. Prevention of Muscle Wasting by CRISPR/Cas9-mediated Disruption of Myostatin In Vivo. Molecular Therapy (2016), 24(11): 1889-1891. (Year: 2016).*
Mendell et al. Duchenne muscular dystrophy: CRISPR/Cas9 treatment. Cell Research (2016), 26:513-514. (Year: 2016).*
Long et al. Prevention of muscular dystrophy in mice by CRISPR/Cas9-mediated editing of germline DNA. Science (2014), 345 (6201): 1184-1188. (Year: 2014).*
Lisa Li et al. Precise Correction of the Dystrophin Gene in Duchenne Muscular Dystrophy Patient Induced Pluripotent Stem Cells by TALEN and CRISPR-Cas9. Stem Cell Reports (2015), vol. 4: 143-154. (Year: 2015).*
Lim et al. Applications of CRISPR/Cas9 for the Treatment of Duchenne Muscular Dystrophy. J. Pers. Med. (2018), 8, 38: 1-20. (Year: 2018).*
Bengtsson et al. Muscle-specific CRISPR/Cas9 dystrophin gene editing ameliorates pathophysiology in a mouse model for Duchenne muscular dystrophy. Nature Communications (2017), 8:14454: 1-9. (Year: 2017).*
Sharma et al. CRISPR-Cas9: A Preclinical and Clinical Perspective for the Treatment of Human Diseases. Molecular Therapy vol. 29 No. 2: 571-586, Feb. 2021. (Year: 2021).*
Mollanoori et al. Promising therapeutic approaches using CRISPR/Cas9 genome editing technology in the treatment of Duchenne muscular dystrophy. Genes & Diseases (2021), 8: 146-156. (Year: 2021).*
Kappel et al. Regulating gene expression in transgenic animals. Current Opinion in Biotechnology, vol. 3, Issue 5, Oct. 1992, pp. 548-553. (Year: 1992).*
Mullins et al. (Perspectives Series: Molecular Medicine in Genetically Engineered Animals. J. Clin. Invest. 97(7): 1557-1560, 1996. (Year: 1996).*
Wigley et al. Site-specific Transgene Insertion: an Approach. Reprod. Fertil. Dev., 1994, 6, 585-8. (Year: 1994).*
Phillips et al. Thechallengeofgenetherapyand DNAdelivery. J. Pharm. Pharmacology 53:1169-1174, 2001 . . . (Year: 2001).*
Gardlik et al. Vectors and delivery systems in gene therapy. Med. Sci. Monit. 11(4): RA110-121, 2005. (Year: 2006).*
Office Action corresponding to U.S. Appl. No. 16/958,244 dated Dec. 9, 2021 (7 pages).
Colombian Office Action for Application No. NC2020/0008212 dated Aug. 31, 2022, 8 pages.
Chinese Office Action for Application No. 201880083465.4, dated Aug. 17, 2022, 14 pages.
Taiwan Office Action for Application No. 107147438, dated Sep. 20, 2022, 8 pages.
Extended European Search Report of Application No. 18896553.7 (dated Sep. 30, 2021).
Extended European Search Report of Application No. 18894951.5 (dated Sep. 30, 2021).
Russian Office Action for Application No. 2020124751, dated Feb. 22, 2022, 16 pages.
U.S. Office Action for U.S. Appl. No. 16/958,244, dated Mar. 4, 2022, 7 pages.
Yin, H. et al. (2016) "Therapeutic genome editing by combined viral and non-viral delivery of CRISPR system components in vivo," Nat. Biotechnol. 34(3):328-333.
Yin, H, et al. (2017) "Structure-guided chemical modification of guide RNA enables potent non-viral in vivo genome editing," Nat. Biotechnol. 35(12):1179-1187.
Tabebordbar, M. et al. (2016) "In vivo editing in dystrophic mouse muscle and muscle stem cells," Science 351(6271):407-411.
Makita, Y, et al. (2017) "Advances in genome editing technologies for treating muscular dystrophy", Clinical Calcium 27(3):391-399. (English Abstract).
Zhang, L. et al (2017) "Lipid nanoparticle-mediated efficient delivery of CRISPR/Cas9 for tumor therapy," NPG Asia Materials (9):e441, 1-8.
Hirosawa, M et al. (2017) "Cell-type-specific genome editing with micro-RNA-responsive CRISPR-Cas9 switch," Nucleic Acid Res. 45(13):e118, 1-11.
Akita, H. et al. (2013) "A Neutral Envelope-Type Nanoparticle Containing pH-Responsive and SS Cleavable Lipid-Like Material as a Carrier for Plasmid DNA," Adv. Healthcare Master 2(8):1120-1125.
International Search Report corresponding to PCT/JP2018/048034 dated Mar. 26, 2019.
International Search Report corresponding to PCT/JP2018/048054 dated Mar. 26, 2019.
Written Opinion corresponding to International Patent Application No. PCT/JP2018/048034, dated Mar. 26, 2019 (7 pages).
1 Brazilian Office Action for Application No. BR112020012424-9, dated Sep. 9, 2022, 6 pages. .
Bastin et al., Salt Selection and Optimisation Procedures for Pharmaceutical New Chemical Entities. Organic Process Research & Development. 2000;4:427-435.
Sun et al., Tailoring non-viral delivery vehicles for transporting genome-editing tools. Sci. China Mat. 2017;60(6):511-5.
Chinese Office Action for Application No. 201880084068.9.4, dated Feb. 22, 2023, 14 pages.

\* cited by examiner

COMPOSITION FOR MODIFYING TARGET GENE

RELATED APPLICATIONS

This application is a national stage application filed under 35 U.S.C. § 371, of International Patent Application No. PCT/JP2018/048034, filed Dec. 27, 2018, which claims the benefit of and priority to JP2017-254798, filed Dec. 28, 2017, the entire contents of which are hereby expressly incorporated by reference herein.

INCORPORATION BY REFERENCE OF SEQUENCE LISTING

The contents of the text file named "PT38-9026US_Sequence Listing.txt", which was created on Jun. 18, 2020 and is 12,288 byte in size, are hereby incorporated by reference in their entireties and for all purposes.

TECHNICAL FIELD

The present invention relates to a composition that enables introduction of a substance used as an active ingredient for CRISPR systems into cells. Further, the present invention relates to a method for inducing gene modification at a target gene locus in a cell with use of such a composition, for example, a method for preventing or treating muscular dystrophy by modifying a dystrophin gene of muscle cells.

BACKGROUND OF INVENTION

Research and development have been made in recent years for gene modification in various cells with use of a genome editing means, such as CRISPR (Clustered, regularly interspaced, short palindromic repeats) systems. However, there are few reports on gene modification by delivering into intended cells a gene modification tool such as a gRNA (guide RNA) and a gene encoding an RNA-guided nuclease (e.g., Cas9), which are required in CRISPR systems, through administration to a living body by injection or the like, and demanded is development of a delivery technique for delivering a gene modification tool capable of providing a high gene modification efficiency, for example, in muscle cells. Class 1 and class 2 CRISPR systems are known, and class 1 is known to include type I, type III, and type IV, and class 2 is known to include type II, type V, and type VI. Cas9, which is of type II of class 2 that binds to a DNA and cleave it, is widely used for gene modification, and Cpf1 (Cas12a) and C2c1 (Cas12b), which are of type V of class 2 that similarly binds to and cleave a DNA, and so on are also used. In addition, Cas13a (C2c2) and Cas13b, which are of type VI of class 2 that binds to an RNA and cleaves it, and so on have been reported.

Lipid nanoparticles (LNPs) capable of encapsulating a nucleic acid such as a gRNA and an mRNA are known as one of means to deliver to cells. Examples of prior art documents describing delivery of a gene modification tool for a CRISPR/Cas9 system to hepatocytes with LNPs are as follows.

Non Patent Literature 1 discloses that an mRNA for SpCas9 (Cas9 derived from *Streptococcus pyogenes*) in an LNP produced by using C12-200 (lipid-like molecule), cholesterol, C14PEG2000 (polyethylene glycol lipid), DOPE (1,2-dioleyl-sn-glycero-3-phosphoethanolamine) and arachidonic acid, and a gRNA and homology-directed repair (HDR) template in an AAV vector were intravenously injected into Fah$^{mut/mut}$ mice, and this resulted in an increased fraction of Fah+ cells in the liver.

Patent Literature 1 describes a lipid particle containing a gRNA, a cationic lipid and a non-cationic lipid. As the cationic lipid, for example, 1,2-dilinoleyloxy-N,N-dimethylaminopropane (DLinDMA) is exemplified. Disclosed in Examples is that an LNP including an mRNA for Cas9 and a gRNA was intravenously injected into mice, and then indel was is found for the Pcsk9 gene and HBV RT gene of hepatocytes.

Non Patent Literature 2 discloses that an mRNA for SpCas9 and a modified sgRNA were intravenously injected into mice with an LNP produced by using cKK-E12 (a lipid-like molecule as a derivative from a lysine-based dipeptide), cholesterol, C14PEG2000 and DOPE, and then indel was found for the Pcsk9 gene, Fah gene and Rosa26 gene of hepatocytes.

On the other hand, examples of prior art documents describing delivery of a gene modification tool for a CRISPR/Cas9 system to muscle cells or the like by means of a non-LNP means are as follows.

Patent Literature 2 describes delivery to muscle cells or the like with use of a virus vector (e.g., adeno-associated virus (AAV)) including a gRNA and a gene encoding Cas9 for the purpose of repairing deletion of a mouse dystrophin gene (Dmd) to treat Duchenne muscular dystrophy. Disclosed in Examples is that recombinant AAV including a vector incorporating an sgRNA to skip exon 23 of Dmd and an spCas9 gene was administered by injection to mdx mice having nonsense mutation (stop codon) in exon 23 of Dmd, and then some of muscle fibers and cardiac muscle cells were found to be dystrophin-positive.

Patent Literature 3 also discloses that a gene such as Dmd can be repaired by delivering a gRNA, a gene encoding Cas9, and so on to muscle cells or the like. Disclosed in Examples (e.g., Examples, 9, 11) is that an expression plasmid incorporating an sgRNA to skip exon 51 of Dmd and an SpCas9 gene was introduced through electroporation into an initial muscle cell population (ex vivo) collected from a patient, and the cell population was then transplanted into an immunodeficient mouse, and as a result dystrophin protein was successfully expressed in the body of the mouse.

Non Patent Literature 3 discloses that a gRNA and an mRNA for SaCas9 or an mRNA for SpCas9 in AAV was intravenously injected or intramuscularly administered to mdx mice (muscular dystrophy model), and then deletion of exon 23 was found in the cardiac muscle and skeletal muscle.

CITATION LIST

Patent Literature

Patent Literature 1: International Publication No. WO 2016/197133
Patent Literature 2: International Publication No. WO 2016/025469
Patent Literature 3: International Publication No. WO 2014/197748

Non Patent Literature

Non Patent Literature 1: Yin et al., Nat. Biotech., 34 (2016) p 329-333
Non Patent Literature 2: Yin et al., Nat. Biotech., 35 (2017) p 1179-1187

Non Patent Literature 3: Tabebordbar et al., Science, 351 (2016) p 407-411

SUMMARY OF INVENTION

Technical Problem

An object of the present invention is to provide a delivery technique for delivering a gene modification tool capable of providing a high gene modification efficiency in various cells.

Solution to Problem

The present inventors have diligently examined to solve the problem, and found that the problem is successfully solved by using a lipid particle formed of a compound represented by a formula below (one of cationic lipids) or a salt thereof and another structural lipid, which enables efficient delivery of guide RNAs (gRNAs), RNA-guided nuclease proteins typified by Cas9 or nucleic acids including a sequence encoding such a protein, and so on into various cells, thus completing the present invention.

Specifically, the present invention relates at least to the followings.

[1]
A composition for inducing gene modification at a target gene locus in a cell, containing:
1) a compound represented by formula (I):

[Formula 1]

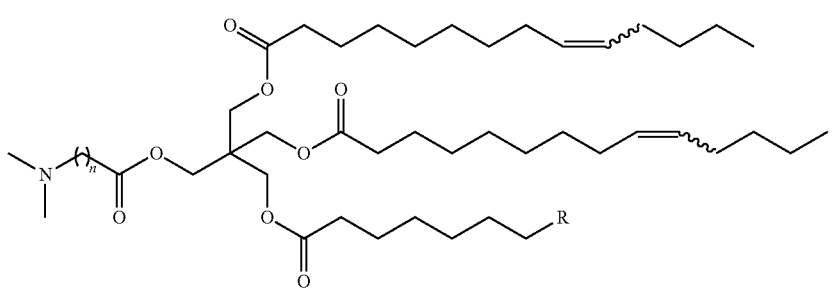

wherein
n represents an integer of 2 to 5,
R represents a linear $C_{1-5}$ alkyl group, a linear $C_{7-11}$ alkenyl group, or a linear $C_{11}$ alkadienyl group, and wavy lines each independently represent a cis-type bond or a trans-type bond,
or a salt thereof;
2) a structural lipid; and
3) a guide RNA or a DNA including a sequence encoding the guide RNA, and/or an RNA-guided nuclease or a nucleic acid including a sequence encoding the RNA-guided nuclease.

[2]
The composition according to item 1, wherein
the RNA-guided nuclease is Cas9; and
the guide RNA is:
(a) a chimeric RNA, or
(b) two or more RNAs including a crRNA and a tracrRNA.

[2a]
The composition according to item 1, wherein the RNA-guided nuclease is Cpf1.

[3]
The composition according to item 1 or 2, wherein the Cas9 is Cas9 derived from *Streptococcus pyogenes*.

[4]
The composition according to any one of items 1 to 3, wherein the guide RNA is two or more types of guide RNAs.

[5]
The composition according to any one of items 1 to 4, wherein the cell is a muscle cell.

[6]
The composition according to any one of items 1 to 5, wherein the target gene locus includes a nucleotide sequence of a dystrophin gene.

[7]
The composition according to any one of items 1 to 6, wherein the guide RNA is:
(1) a chimeric RNA including a nucleic acid sequence represented by SEQ ID NO: 1 or SEQ ID NO: 2; or
(2) (i) a crRNA including a nucleic acid sequence represented by SEQ ID NO: 3 or SEQ ID NO: 4, and
(ii) a tracrRNA including a nucleic acid sequence represented by SEQ ID NO: 7 or SEQ ID NO: 8.

[8]
A method for modifying a target gene locus in a cell, including a step of contacting the composition according to item 1 with a cell.

[9]
The method according to item 8, wherein
the RNA-guided nuclease is Cas9; and
the guide RNA is:
(a) a chimeric RNA, or
(b) two or more RNAs including a crRNA and a tracrRNA.

[9a]
The method according to item 8, wherein the RNA-guided nuclease is Cpf1.

[10]
The method according to item 8 or 9, wherein the Cas9 is Cas9 derived from *Streptococcus pyogenes*.

[11]
The method according to any one of items 8 to 10, wherein the cell is a muscle cell.

[12]
The method according to any one of items 8 to 11, wherein the target gene locus includes a nucleotide sequence of a dystrophin gene.

[13]
The method according to any one of items 8 to 12, wherein the guide RNA is:

(1) a chimeric RNA including a nucleic acid sequence represented by SEQ ID NO: 1 or SEQ ID NO: 2; or
(2) (i) a crRNA including a nucleic acid sequence represented by SEQ ID NO: 3 or SEQ ID NO: 4, and
(ii) a tracrRNA including a nucleic acid sequence represented by SEQ ID NO: 7 or SEQ ID NO: 8.

[14]
A cell with a modified target gene locus, wherein the cell is obtained through the method according to any one of items 8 to 13.

[15]
A drug containing the composition according to item 6.

[16]
The drug according to item 15, wherein
the RNA-guided nuclease is Cas9; and
the guide RNA is:
(a) a chimeric RNA, or
(b) two or more RNAs including a crRNA and a tracrRNA.

[16a]
The medicament according to item 15, wherein the RNA-guided nuclease is Cpf1.

The medicament according to item 15 or 16, wherein the Cas9 is Cas9 derived from *Streptococcus pyogenes*.

[18]
The medicament according to any one of items 15 to 17, wherein the guide RNA is:
(1) a chimeric RNA including a nucleic acid sequence represented by SEQ ID NO: 1 or SEQ ID NO: 2; or
(2) (i) a crRNA including a nucleic acid sequence represented by SEQ ID NO: 3 or SEQ ID NO: 4, and
(ii) a tracrRNA including a nucleic acid sequence represented by SEQ ID NO: 7 or SEQ ID NO: 8.

[19]
The medicament according to any one of items 15 to 18, which is an agent for the prophylaxis or treatment of muscular dystrophy.

[20]
The medicament according to items 15 to 19, which is an agent for producing a repaired dystrophin protein.

[21]
A method for preventing or treating muscular dystrophy in a mammal, wherein an effective amount of the composition according to item 6 or 7 is administered to the mammal.

[21a]
The method according to item 21, wherein the administration is intravenous administration.

[21b]
The method according to item 21, wherein the administration is intramuscular administration.

[22]
A method for producing repaired dystrophin protein in a mammal, wherein an effective amount of the composition according to item 6 or 7 is administered to the mammal.

[23]
Use of the composition according to item 6 or 7 for producing a prophylactic or therapeutic agent for muscular dystrophy.

[24]
The composition according to item 6 or 7 for use in prevention or treatment of muscular dystrophy.

[25]
A method for producing a cell with a modified target gene locus, including a step of contacting the composition according to any one of items 1 to 7 with a cell.

[26]
A method for producing a non-human mammal with a modified target gene locus, including the steps of:
(1) contacting the composition according to any one of items 1 to 7 with a fertilized ovum, embryonic stem cell, or oocyte of a non-human mammal;
(2) selecting a fertilized ovum, embryonic stem cell, or oocyte with a modified target gene locus; and
(3) transplanting the selected fertilized ovum, embryonic stem cell, or oocyte into a female animal of a non-human mammal.

[27]
A method for producing a composition for inducing gene modification at a target gene locus in a cell, including a step of mixing a lipid particle dispersion and an aqueous solution together, wherein
the lipid particle dispersion contains:
1) a compound represented by formula (I):

[Formula 2]

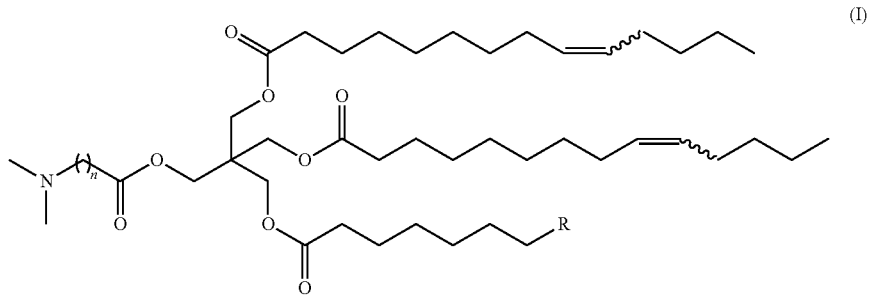

wherein
n represents an integer of 2 to 5,
R represents a linear $C_{1-5}$ alkyl group, a linear $C_{7-11}$ alkenyl group, or a linear $C_{11}$ alkadienyl group, and
wavy lines each independently represent a cis-type bond or a trans-type bond,
or a salt thereof; and
2) a structural lipid, and
the aqueous solution contains:
3) a guide RNA or a DNA including a sequence encoding the guide RNA, and/or an RNA-guided nuclease or a nucleic acid including a sequence encoding the RNA-guided nuclease.

[28]
The method according to item 27, wherein the guide RNA is two or more types of guide RNAs.

Herein, "the compound represented by formula (I)" is occasionally referred to as "compound (I)". "The compound represented by formula (I) or a salt thereof" is occasionally called "the compound of the present invention". A "lipid particle containing the compound represented by formula (I) or a salt thereof (the compound of the present invention)" is occasionally called "the lipid particle of the present invention". "A guide RNA or a DNA including a sequence encoding the guide RNA, and/or an RNA-guided nuclease or a nucleic acid including a sequence encoding the RNA-guided nuclease" is occasionally called "the active ingredient of the present invention". "A guide RNA or a DNA including a sequence encoding the guide RNA" is occasionally called "a gRNA or the like", and "an RNA-guided nuclease or a nucleic acid including a sequence encoding the RNA-guided nuclease" is occasionally called "an RNA-guided nuclease or the like". A composition containing the compound of the present invention, a structural lipid, a gRNA or the like, and an RNA-guided nuclease or the like is occasionally called "the composition of the present invention".

The shape of the lipid particle of the present invention is not limited to a particular shape, and the scope includes a complex in which the compound of the present invention and so on assemble to form a sphere; a complex in which the compound of the present invention and so on assemble without forming a particular shape; a complex in which the compound of the present invention and so on dissolve in a solvent; and a complex in which the compound of the present invention and so on homogeneously or heterogeneously disperse in a dispersion medium.

Advantageous Effects of Invention

The present invention enables introduction of a gRNA or the like and an RNA-guided nuclease or the like to be used as an active ingredient for CRISPR systems into various cells, tissues, or organs.

Figure 4:
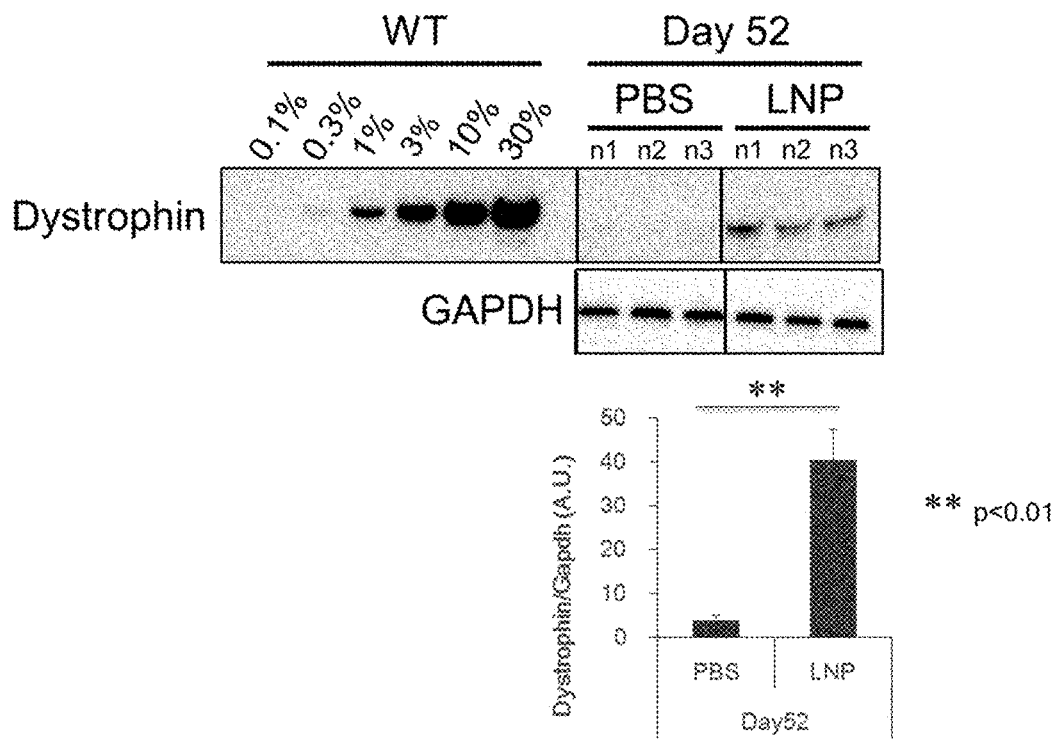
FIG. 4 shows the expression levels of dystrophin protein (relative values of dystrophin/Gapdh) calculated from Western blotting and concentrations therein as results of "Evaluation of Dystrophin Protein Recovery in Skeletal Muscle" in [2-6] of Example 2.
Figure 8:
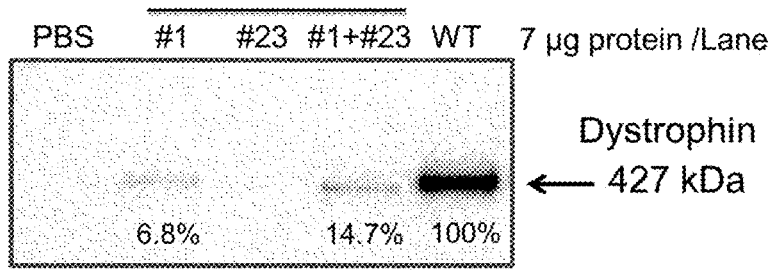
FIG. 8 shows the expression levels of dystrophin protein (relative values of dystrophin/GAPDH) calculated from Western blotting and concentrations therein as results of "Evaluation of Dystrophin Protein Recovery in Human iPS Cell-Derived Myoblasts" in [4-6] of Example 4.

The dystrophin proteins shown in FIGS. 4 and 8 each represent repaired dystrophin protein (a human dystrophin protein translated from an mRNA formed by linking exon 43 and exon 46).

DETAILED DESCRIPTION OF INVENTION

Definitions of substituents used herein are described below in detail. Substituents have the following definitions, unless otherwise stated.

Examples of the "linear $C_{1-5}$ alkyl group" herein include methyl, ethyl, propyl, butyl, and pentyl.

Examples of the "linear $C_{7-11}$ alkenyl group" herein include 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, and 10-undecenyl. While each of these linear $C_{7-11}$ alkenyl groups has one carbon-carbon double bond, and hence the carbon-carbon double bond can form a cis-type structure and a trans-type structure, the carbon-carbon double bond may form any of the structures.

Examples of the "linear $C_{11}$ alkadienyl group" herein include 1,3-undecadienyl, 1,4-undecadienyl, 1,5-undecadienyl, 1,6-undecadienyl, 1,7-undecadienyl, 1,8-undecadienyl, 1,9-undecadienyl, 1,10-undecadienyl, 2,4-undecadienyl, 2,5-undecadienyl, 2,6-undecadienyl, 2,7- undecadienyl, 2,8-undecadienyl, 2,9-undecadienyl, 2,10-undecadienyl, 3,5-undecadienyl, 3,6-undecadienyl, 3,7-undecadienyl, 3,8-undecadienyl, 3,9-undecadienyl, 3,10-undecadienyl, 4,6-undecadienyl, 4,7-undecadienyl, 4,8-undecadienyl, 4,9-undecadienyl, 4,10-undecadienyl, 5,7-undecadienyl, 5,8-undecadienyl, 5,9-undecadienyl, 5,10-undecadienyl, 6,8-undecadienyl, 6,9-undecadienyl, 6,10-undecadienyl, 7,9-undecadienyl, 7,10-undecadienyl, and 8,10-undecadienyl. While each of these linear $C_{11}$ alkadienyl groups has two carbon-carbon double bonds, and hence the carbon-carbon double bonds can each independently form a cis-type structure and a trans-type structure, each carbon-carbon double bond may form any of the structures.

Preferred examples of n and the wavy lines in formula (I) are as follows.

n is preferably an integer of 3 to 5, and more preferably 3.

The wave lines are preferably each a cis-type bond.

Specific preferred examples of compound (I) are as follows.

Compound (A): such a compound that n is an integer of 3 to 5, R is a linear $C_{7-11}$ alkenyl group in a cis-type structure, and the wavy lines are each a cis-type bond.

Compound (B): such a compound that n is 4, R is a linear $C_{11}$ alkadienyl group in which two carbon-carbon double bonds each form a cis-type structure, and the wavy line are each a cis-type bond.

Compound (C): such a compound that n is 2 or 3, R is a linear $C_{1-5}$ alkyl group, and the wavy lines are each a cis-type bond.

Specific, more preferred examples of compound (I) are as follows.

Compound (A1): a compound wherein n is an integer of 3 to 5, R is 5-heptenyl, 7-nonenyl, or 9-undecenyl in the cis-type structure, and the wavy lines are each a cis-type bond.

Compound (B1): a compound wherein n is 4, R is 2,5-undecadienyl in which two carbon-carbon double bonds each form a cis-type structure, and the wavy lines are each a cis-type bond.

Compound (C1): a compound wherein n is 2 or 3, R is methyl, propyl, or pentyl, and the wavy lines are each a cis-type bond.

A specific more preferred example of compound (I) is 3-((4-(dimethylamino)butanoyl)oxy)-2,2-bis(((9Z,9'Z)-tetradec-9-enoyloxy)methyl)propyl(9Z)-tetradec-9-enoate.

The salt of compound (I) is preferably a pharmacologically acceptable salt, and examples thereof include salts with an inorganic base, salts with an organic base, salts with an inorganic acid, salts with an organic acid, and salts with a basic or acidic amino acid.

Preferred examples of salts with an inorganic base include alkali metal salts such as sodium salts and potassium salts; alkali earth metal salts such as calcium salts and magnesium salts; aluminum salts; and ammonium salts. Preferred are sodium salts, potassium salts, calcium salts, and magnesium salts, and more preferred are sodium salts and potassium salts.

Preferred examples of salts with an organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, and N,N-dibenzylethylenediamine.

Preferred examples of salts with an inorganic acid include salts with hydrofluoric acid, hydrochloric acid, hydrobromic acid, hydroiodic acid, nitric acid, sulfuric acid, and phosphoric acid. Preferred are salts with hydrochloric acid and salts with phosphoric acid.

Preferred examples of salts with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, and p-toluenesulfonic acid.

Preferred examples of salts with a basic amino acid include salts with arginine, lysine, and ornithine.

Preferred examples of salts with an acidic amino acid include salts with aspartic acid and glutamic acid.

In a typical mode of the present invention, the compound of the present invention is forming a lipid particle together with a structural lipid. In the composition of the present invention, the lipid particle includes a guide RNA or a DNA including a sequence encoding the guide RNA, and/or an RNA-guided nuclease or a nucleic acid including a sequence encoding the RNA-guided nuclease.

The structural lipid is not limited to a particular structural lipid if that is capable of forming a lipid particle after being mixed with the compound of the present invention to prepare a mixed lipid component. For such a structural lipid, for example, at least one selected from the group consisting of the following may be used: sterols (e.g., cholesterol, cholesteryl ester, cholesteryl hemisuccinate); phospholipids (e.g., phosphatidylcholine (e.g., dipalmitoylphosphatidylcholine, distearoylphosphatidylcholine, lysophosphatidylcholine, dioleoylphosphatidylcholine, palmitoyloleoylphosphatidylcholine, dilinolenoylphosphatidylcholine, MC-1010 (NOF CORPORATION), MC-2020 (NOF CORPORATION), MC-4040 (NOF CORPORATION)), phosphatidylserine (e.g., dipalmitoylphosphatidylserine, distearoylphosphatidylserine, dioleoylphosphatidylserine, palmitoyloleoylphosphatidylserine), phosphatidylethanolamine (e.g., dipalmitoylphosphatidylethanolamine, distearoylphosphatidylethanolamine, dioleoylphosphatidylethanolamine, palmitoyloleoylphosphatidylethanolamine, lysophosphatidylethanolamine), phosphatidylinositol, phosphatidic acid); and polyethylene glycol lipids (PEG lipids) (e.g., PEG-DAA, PEG-DAG, PEG-phospholipid conjugate, PEG-Cer, PEG-cholesterol, PEG-C-DOMG, 2KPEG-CMG, GM-020 (NOF CORPORATION), GS-020 (NOF CORPORATION), GS-050 (NOF CORPORATION)). In the present invention, it is preferred to use all of the three, namely, a sterol (in particular, cholesterol), a phospholipid (in particular, phosphatidylcholine), and a polyethylene glycol lipid, as the structural lipid.

The ratio between the compound of the present invention and the structural lipid in the composition of the present invention may be appropriately controlled according to the purpose. For example, if a lipid particle is formed of a mixed lipid component containing the compound of the present invention and the structural lipid in the composition of the present invention, the ratio of the structural lipid is typically 0.008 to 4 mol and preferably 0.4 to 1.5 mol per 1 mol of the compound of the present invention. In another definition of ratios, the amount of the compound of the present invention is typically 1 to 4 mol, that of the sterol is typically 0 to 3 mol, that of the phospholipid is typically 0 to 2 mol, and that of the polyethylene glycol lipid is typically 0 to 1 mol in the mixed lipid component. In a more preferred embodiment with use of a mixture of the compound of the present invention and additional lipid components, with respect to ratios, the amount of the compound of the present invention is 1 to 1.5 mol, that of the sterol is 0 to 1.25 mol, that of the phospholipid is 0 to 0.5 mol, and that of the polyethylene glycol lipid is 0 to 0.125 mol.

The active ingredient of the present invention is described below.

In the present invention, a substance for inducing gene modification at a target gene locus in a cell, specifically, a guide RNA or a DNA including a sequence encoding the guide RNA, and/or an RNA-guided nuclease or a nucleic acid including a sequence encoding the RNA-guided nuclease each of which is compatible with CRISPR systems are/is used as an active ingredient. Fundamental matters on substances compatible with CRISPR systems for gene modification are well known and matters on various applications are currently known, and those well-known or known matters may be applied to the present invention (e.g., see Citation List shown above). Those skilled in the art could make suitable design, selection, and production according to the purpose with respect to a target gene locus and each component of a CRISPR system.

Any cells and target gene locus may be appropriately selected, without any limitation, according to the purpose of gene modification, but cells and a target gene locus that are involved in a genetic disease and can be a subject of gene therapy are typically selected.

The composition of the present invention may be used for introduction of an active ingredient into various types of cells, tissues, or organs. Examples of cells to which the present invention may be applied include mesenchymal stem cells, neural stem cells, skin stem cells, splenocytes, nerve cells, glial cells, pancreatic B cells, bone marrow cells, mesangial cells, Langerhans cells, epidermal cells, epithelial cells, endothelial cells, fibroblasts, fiber cells, muscle cells (e.g., skeletal muscle cells, cardiac muscle cells, myoblasts, muscle satellite cells, smooth muscle cells), fat cells, blood cells (e.g., macrophages, T cells, B cells, natural killer cells, mast cells, leukocytes, neutrophils, basophils, eosinophils, monocytes, megakaryocytes, hematopoietic stem cells), synoviocytes, chondrocytes, osteocytes, osteoblasts, osteoclasts, mammary cells, hepatocytes or stromal cells, ova, spermatids, or precursor cells capable of inducing differentiation into these cells, stem cells (e.g., including induced pluripotent stem cells (iPS cells), embryonic stem cells (ES cells)), primordial germ cells, oocytes, and fertilized ova. Examples of tissues or organs to which the present invention may be applied include all tissues or organs in which the above cells are present, for example, brain, sites of brain (e.g., olfactory bulb, amygdala, basal ganglion, hippocampus, thalamus, hypothalamus, subthalamic nucleus, cerebral cortex, medulla oblongata, cerebellum, occipital lobe, frontal lobe, temporal lobe, putamen, caudate nucleus, callosum, substantia nigra), spinal cord, pituitary gland, stomach, pancreas, kidney, liver, gonad, thyroid, gallbladder, bone marrow, adrenal gland, skin, lung, digestive tract (e.g., large intestine, small intestine), blood vessel, heart, thymus, spleen, submandibular gland, peripheral blood, peripheral blood cells, prostate, placenta, uterus, bones, joints, and muscles. Those cells, tissues, or organs may be cancer cells, cancer tissues, or the like that have undergone canceration.

In a preferred mode of the present invention, the cells are muscle cells (e.g., cardiac muscle cells, skeletal muscle cells, muscle satellite cells), fibroblasts, mesenchymal stem cells, blood cells, or iPS cells, and more preferably muscle cells (especially, skeletal muscle cells or muscle satellite cells). Examples of such muscle cells include muscle cells collected from a human (a patient or a healthy individual) or a mammal other than humans (e.g., a disease model animal of a non-human primate (e.g., a cynomolgus monkey, a rhesus monkey, a chimpanzee), a cattle, a pig, a mouse, a rat, or the like), muscle cells in a living body (e.g., in a living body of a human), a muscle cell line, and muscle cells differentiated from stem cells (e.g., iPS cells, ES cells).

In a preferred mode of the present invention, the target gene locus includes the nucleotide sequence of a dystrophin gene.

A dystrophin gene is a huge gene that is present on the X chromosome and formed of more than 2200000 nucleotides. There are various isoforms with different transcription start sites, and known examples are Dp71, which is systemically expressed, Dp116, which is expressed in peripheral nerve cells, Dp140, which is expressed in the brain and kidney, Dp260, which is expressed in the retina, Dp417p, which is expressed in Purkinje neurons, Dp427b, which is expressed in the brain, and Dp427m, which is expressed in skeletal muscles. Especially, a dystrophin protein produced from the isoform Dp427m is a protein that is primarily expressed in muscle cells and binds at an actin-binding domain present in the N-terminal side to cytoskeletal actin and also binds at a cysteine-rich domain present in the C-terminal side to a dystroglycan complex, constituting the cytoskeleton together with actin. The dystrophin gene of the isoform Dp427m is composed of 79 exons.

In patients with Duchenne muscular dystrophy, almost no functional dystrophin protein is expressed (protein levels of 3% or lower of those for healthy individuals as detected with Western blotting) because of the presence of deletion or duplication mutation of any exon of a dystrophin gene, or of point mutation (nonsense mutation) or indel mutation (frameshift mutation) of a nucleotide in an exon. In patients with Becker's muscular dystrophy, which is relatively milder than Duchenne muscular dystrophy, on the other hand, a dystrophin protein with a shorter amino acid sequence than normal dystrophin proteins or with substitution of some amino acids is expressed if no intervening stop codon is generated even when deletion of an exon or point mutation of a nucleotide is present.

Deletion of single or multiple exons accounts for half or more of cases of mutation of a dystrophin gene in Duchenne muscular dystrophy and Becker's muscular dystrophy. The site between exon 44 and exon 55 is known as a site in which deletion is particularly frequently found. Which exon should be subjected to exon skipping in order to express an appropriate repaired dystrophin can be determined by referring to previously-reported articles or the like in view of the deleted exon site of a dystrophin gene (e.g., van Deutekom J C, van Ommen G J., Nat Rev Genet. 2003). Expression of a repaired dystrophin with genome editing can be achieved, not only through exon skipping, but also through a method of introducing micro deletion or insertion into a dystrophin gene to control the reading frame, or through insertion of a deleted exon by homologous recombination or the like.

When an abnormality is present in a dystrophin gene as described above, the abnormality can be corrected with any of the following operations: (i) one or two or more exons are excluded (skipped) from an mRNA to link together exons before and after the excluded exon(s) so as not to cause frameshift; (ii) one or two or more nucleotides are inserted or deleted to correct frameshift; (iii) a deleted exon is knocked-in, and so on. In the case of (i) or (ii), a dystrophin protein with a shorter or longer amino acid sequence than normal dystrophin proteins or with substitution of some amino acids is produced. With (ii) or (iii), a normal dystrophin protein can be produced. Such correction of the dystrophin gene enables prevention or treatment of diseases including muscular dystrophy.

The nucleotide sequence of the human dystropin gene is available, for example, from National Center for Biotechnology information.

The guide RNA may be in the form of a single RNA formed of a crRNA and a tracrRNA linked together, that is, a chimeric RNA (occasionally called a single guide RNA or an sgRNA), or in the form of single RNAs that are not linked together (a combination of two RNAs, or a combination of two or more RNAs). The composition of the present invention may contain such a guide RNA in the form of an RNA as it is, or in the form of a DNA including a sequence encoding a guide RNA (e.g., an expression plasmid).

The guide RNA may be in a form targeting one nucleotide sequence (a single sgRNA, or a pair of a crRNA and a tracrRNA), or in a form targeting two or more nucleotide sequences (two or more sgRNAs, or a combination of two or more pairs of a crRNA and a tracrRNA). Herein, "type" of the guide RNA is occasionally set forth for each nucleotide sequence targeted. Accordingly, the guide RNA in a form targeting two or more nucleotide sequences is herein occasionally referred to as "two or more types of guide RNAs". The guide RNA is preferably of two types or two or more types.

In using two or more types of guide RNAs, the distance between nucleotide sequences targeted by these guide RNAs is not limited, but it is preferable for the target sequences for the two guide RNAs not to overlap. It is preferable that the target sequences for the two guide RNAs be separated by one or more nucleotides.

In using two types of guide RNAs, it is preferable that positions of DNA cleavage generated by a CRISPR system using these two types of guide RNAs cover a target gene locus or a specific nucleotide sequence in a target gene locus in a cell for which gene modification is induced. Covering a nucleotide sequence here means that a position of DNA cleavage is present in each of the upstream and downstream of the nucleotide sequence.

In using two types of guide RNAs, the target sequences for the two types of guide RNAs are not limited to particular sequences, and may be, for example, nucleotide sequences with which target recognition sequences of SEQ ID NO: 3 and SEQ ID NO: 4 are hybridizable.

The crRNA of the present invention includes a nucleic acid sequence that is formed of about 18 to 20 nucleotides and hybridizable with a specific nucleotide sequence (herein, occasionally referred to as the "target sequence") in a target gene locus in a cell (herein, occasionally referred to as the "target recognition sequence"). The target recognition sequence is preferably a nucleic acid sequence represented by SEQ ID NO: 3 or SEQ ID NO: 4. In a preferred mode of the present invention, the crRNA includes a nucleic acid sequence represented by SEQ ID NO: 3 or SEQ ID NO: 4. In a preferred mode of the present invention, the crRNA includes a nucleic acid sequence represented by SEQ ID NO: 5 or SEQ ID NO: 6. The target sequence is adjacent to a short sequence recognized by CRISPR systems (PAM (protospacer adjacent motif)). Conditions for the sequence and length of PAM depend on the type of nuclease to be used, and PAM is typically a sequence that is formed of 2 to 5 base pairs and adjacent to the target sequence.

In a preferred mode of the present invention, the guide RNA is a chimeric RNA (sgRNA) including a nucleic acid sequence represented by SEQ ID NO: 1 or SEQ ID NO: 2.

In a preferred mode of the present invention, the guide RNA is a combination of (i) a crRNA including a nucleic acid sequence represented by SEQ ID NO: 3 or SEQ ID NO: 4 and (ii) a tracrRNA including a nucleic acid sequence represented by SEQ ID NO: 7 or SEQ ID NO: 8.

```
SEQ ID NO: 1: Total sequence of sgRNA
corresponding to "HsDMDEx45#1" in Examples
5'-U(M)^G(M)^G(M)^UAUCUUACAGGCUCCGUUUUAGAGCUAG

UAGCGUUAUAAGGCUAGUCCGUUAUCAACUUGAAAAAGUGGCACCG

AGUCGG(M)^U(M)^G(M)^C-3'

SEQ ID NO: 2: Total sequence of sgRNA
corresponding to "HsDMDEx45#23" in Examples
5'-A(M)^G(M)^C(M)^UGUCAGACAGAAGGUUUUAGAGCUAGUA

GCGUUAUAAGGCUAGUCCGUUAUCAACUUGAAAAAGUGGCACCGAG

UCGG(M)^U(M)^G(M)^C-3'

SEQ ID NO: 3: Target recognition sequence in
SEQ ID NO: 1
5'-U(M)^G(M)^G(M)^UAUCUUACAGGAACUCC-3'

SEQ ID NO: 4: Target recognition sequence in
SEQ ID NO: 2
5'-A(M)^G(M)^C(M)^UGUCAGACAGAAAAAAG-3'

SEQ ID NO: 5: crRNA Sequence in SEQ ID NO: 1
5'-U(M)^G(M)^G(M)^UAUCUUACAGGAACUCCGUUUUAGAGCU
A-3'

SEQ ID NO: 6: crRNA Sequence in SEQ ID NO: 2
5'-A(M)^G(M)^C(M)^UGUCAGACAGAAAAAAGGUUUUAGAGCU
A-3'

SEQ ID NO: 7: tracrRNA Sequence in SEQ ID
NO: 1
5'-UAGCAAGUUAAAAUAAGGCUAGUCCGUUAUCAACUUGAAAAAG

UGGCACCGAGUCGG(M)^U(M)^G(M)^C-3'

SEQ ID NO: 8: tracrRNA Sequence in SEQ ID
NO: 2
5'-UAGCAAGUUAAAAUAAGGCUAGUCCGUUAUCAACUUGAAAAAG

UGGCACCGAGUCGG(M)^U(M)^G(M)^C-3'
```

In SEQ ID NOs: 1 to 8, each ribose with "(M)" just in the right may be natural (non-modified) ribose, or 2'-O-methylribose or another type of modified ribose, but is preferably 2'-O-methylribose.

In SEQ ID NOs: 1 to 8, each bond, denoted as "^", between 2'-O-methylribose and 2'-O-methylribose or between 2'-O-methylribose and ribose may be a phosphodiester bond or a phosphorothioate bond, but is preferably a phosphorothioate bond.

The target recognition sequence of the present invention has a sequence substantially identical to a nucleic acid sequence represented by any of SEQ ID NOs: 3 and 4 shown above. The crRNA and chimeric RNA (sgRNA) of the present invention each has a sequence substantially identical to a nucleic acid sequence represented by any of SEQ ID NOs: 1, 2, 5, and 6 shown above in the sequence except the target recognition sequence. The tracrRNA of the present invention has a sequence substantially identical to a nucleic acid sequence represented by any of SEQ ID NOs: 7 and 8 shown above. Here, "a sequence substantially identical to . . . " refers to a sequence having a sequence identity of at least approximately 75%. Accordingly, each of the target recognition sequence, crRNA, tracrRNA, and chimeric RNA (sgRNA) of the present invention may have a sequence identity of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% to the sequence represented by the corresponding sequence number as described above. The sequence identity is preferably at least 85% or 90%, more preferably at least 95% or 97%, and particularly preferably at least 99%.

The term "sequence identity" refers to the fraction (%) of base pairs matching between two gene sequences when the sequences are aligned so that the number of base pairs matching therebetween is maximized.

Sequence identity may be determined by using any method known to those skilled in the art. For example, sequence identity may be determined by using Clustal (Gene 73, 1,237-244, 1988), which is multiple sequence alignment program proposed by Higgins et al. The program Clustal is available, for example, from a website of European Bioinformatics Institute (EBI) on the Internet.

Examples of the RNA-guided nuclease to be used in the present invention include RNA-guided endonuclease.

The RNA-guided endonuclease includes at least one nuclease domain and at least one domain that interacts with the gRNA. The RNA-guided endonuclease is guided to a target site of a genome by the gRNA.

The RNA-guided endonuclease may be derived from a clustered regularly interspersed short palindromic repeats (CRISPR)/CRISPR-associated (Cas) system. The CRISPR/Cas system may be of type I, type III, or type IV of class 1, or type II, type V, or type VI of class 2. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, Cas12a (or Cpf1), Cas12b (or C2c1), Cas12c, Cas13a1 (or C2c2), Cas13a2, Cas13b, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

In an embodiment, the RNA-guided endonuclease is derived from the CRISPR/Cas system of type II of class 2. In a specific embodiment, the RNA-guided endonuclease is derived from Cas9 protein. The Cas9 protein may be derived from *Streptococcus pyogenes*, *Streptococcus thermophilus*, the genus *Streptococcus*, *Staphylococcus aureus*, the genus *Staphylococcus*, *Nocardiopsis dassonvillei*, *Streptomyces pristinaespiralis*, *Streptomyces viridochromogenes*, *Streptosporangium roseum*, *Alicyclobacillus acidocaldarius*, *Bacillus pseudomycoides*, *Bacillus selenitireducens*, *Exiguobacterium sibiricum*, *Francisella novicida*, *Lactobacillus delbrueckii*, *Lactobacillus salivarius*, *Geobacillus stearothermophilus*, *Microscilla marina*, *Burkholderia bacteria*, *Polaromonas naphthalenivorans*, *Polaromonas* sp., *Crocosphaera watsonii*, the genus *Cyanothece*, *Microcystis aeruginosa*, the genus *Synechococcus*, *Acetohalobium arabaticum*, *Ammonifex degensii*, *Caldicellulosiruptor becscii*, *Campylobacter jejuni*, *Campylobacter coli*, *Neisseria meningitides*, *Candidatus Desulforudis*, *Clostridium botulinum*, *Clostridium difficile*, *Finegoldia magna*, *Natranaerobius thermophilusm*, *Pelotomaculum thermopropionicum*, *Acidithiobacillus caldus*, *Acidithiobacillus ferrooxidans*, *Allochromatium vinosum*, the genus *Marinobacter*, *Nitrosococcus halophilus*, *Nitrosococccus watsoni*, *Pseudoalteromonas haloplanktis*, *Ktedonobacter racemifer*, *Methanohalbium evestigatum*, *Anabaena variabilis*, *Nodularia spumigena*, the genus *Nostoc*, *Arthrospira Maxima*, *Arthrospira platensis*, the genus *Arthrospira*, the genus *Lyngbya*, *Microcoleus chthonoplastes*, the genus *Oscillatoria*, *Petrotoga mobilis*, *Thermosipho africanus*, or *Acaryochloris marina*.

In an embodiment, the RNA-guided endonuclease is derived from the CRISPR-Cas12a/Cpf1 system of type V of class 2. In a specific embodiment, the RNA-guided endonuclease is derived from Cpf1 protein. The Cpf1 protein may be derived from Acidaminococcus, Lachnospiraceae, *Chlamydomonas reinhardtii*, or *Francisella novicida*.

The CRISPR/Cas protein may be wild-type CRISPR/Cas protein, modified CRISPR/Cas protein, or a fragment of wild-type or modified CRISPR/Cas protein. The CRISPR/Cas protein may be modified to enhance the binding affinity with and/or specificity to nucleic acids, alter the enzymatic activity, or alter other properties of the protein.

The RNA-guided nuclease may be Cas nuclease or Cas nickase. Here, the Cas nuclease or Cas nickase refers to a protein component essential for CRISPR/Cas systems, which is an endonuclease or nickase that exhibits activity once it forms a complex with two RNAs called a CRISPR RNA (crRNA) and a trans-activating crRNA (tracrRNA). A nickase refers to a DNA cleavage enzyme that nicks only one DNA strand. The Cas9 protein generally includes at least two nuclease (i.e., DNase) domains. For example, the Cas9 protein may include an RuvC-like nuclease domain and an HNH-like nuclease domain. In order to cleave a duplex of DNA, the RuvC and HNH domains cooperate to cleave a single strand (Jinek et al., Science, 337: 816-821). In a certain embodiment, the Cas9-derived protein may be modified to include only one functional nuclease domain (either one of an RuvC-like nuclease domain and an HNH-like nuclease domain). For example, the Cas9-derived protein may be modified to delete or mutate so that one of the nuclease domains no longer functions (i.e., lacking nuclease activity). In an embodiment in which one of the nuclease domains is inactive, the Cas9-derived protein is capable of introducing a nick to a double-stranded nucleic acid, but incapable of cleaving a double-stranded DNA. For example, conversion from aspartic acid to alanine in the RuvC-like domain (D10A) converts the Cas9-derived protein to a nickase. Likewise, conversion of histidine to alanine in the HNH domain (H840A or H839A) converts the Cas9-derived protein to a nickase. Each nuclease domain may be modified by using a well-known method such as site-specific mutagenesis, PCR-mediated mutagenesis, and total gene synthesis, and other methods known in the art.

In particular, Cas nuclease or Cas nickase derived from *Streptococcus* sp. or *Staphylococcus* sp., *Francisella novicida*, or *Campylobacter jejuni* may be used for the RNA-guided nuclease. Preferred among them as the origin is *Streptococcus pyogenes* (*S. pyogenes*) for *Streptococcus* sp., and *Staphylococcus aureus* (*S. aureus*) for *Staphylococcus* sp. Cas9 nuclease or Cas9 nickase derived from *Streptococcus pyogenes* recognizes NGG or NAG trinucleotide as a PAM sequence.

The composition of the present invention may contain such an RNA-guided nuclease in the form of protein, or in the form of a nucleic acid (e.g., an mRNA or a DNA such as an expression plasmid) including a nucleotide sequence encoding the amino acid sequence of the protein.

Cas9 is preferred as the RNA-guided nuclease. In a preferred mode of the present invention, the Cas9 is Cas9 derived from *Streptococcus pyogenes* (*S. pyogenes*) (SpCas9). Cas9 variants derived from various bacteria or archaea are known, and not only SpCas9 but also Cas9 having a desired nuclease activity such as Cas9 derived from *Staphylococcus aureus* (*S. aureus*) (SaCas9) may be used in the present invention.

The ratio of the active ingredient of the present invention to the compound of the present invention and the structural lipid (or a lipid particle formed of them) in the composition of the present invention may be appropriately controlled according to the purpose and the type of the active ingredient. If a mixed lipid component containing the compound of the present invention and the structural lipid is forming a lipid particle in the composition of the present invention and an RNA is included as the active ingredient of the present invention in the lipid particle, for example, the ratio of the mass of the active ingredient of the present invention to the mass of the lipid particle (i.e., the total mass of the compound of the present invention and the structural lipid) is typically 1 to 20% by mass, and preferably 2 to 10% by mass.

"RNA" (ribonucleic acid), "DNA" (deoxyribonucleic acid), and "nucleic acid" may each include only natural ribonucleotide or deoxyribonucleotide, or additionally include, as necessary, a nucleotide analog formed by modifying a part of the structure of the molecule, for example, to improve nuclease resistance, to stabilize, to improve affinity with the complementary nucleic acid, or to improve cell permeability. Examples of the nucleotide analog include a sugar-modified nucleotide (e.g., 2'-O-methylribose, 2'-O-propylribose, 2'-O-methoxyethoxyribose, 2'-O-methoxyethylribose, 2'-O-[2-(guanidinium)ethyl]ribose, 2'-O-fluororibose); a bridged artificial nucleic acid (BNA) (e.g., a locked artificial nucleic acid (LNA), an ethylene bridged artificial nucleic acid (ENA)); and a phosphodiester bond-modified nucleotide (e.g., a product with a phosphodiester bond substituted with a phosphorothioate bond, a product with a phosphodiester bond substituted with an N3'-P5' phosphoramidate bond). Nucleic acid may be, for example, a derivative with 5'-polyamine added, a derivative with cholesterol added, a derivative with steroid added, a derivative with bile acid added, a derivative with vitamin added, a derivative with fluorescent dye added, or a derivative with biotin added. "RNA", "DNA", and "nucleic acid" may be each single-stranded or double-stranded.

In a mode of the present invention, it is preferable that at least a part of the guide RNA be the nucleotide analog. Sugar-modified nucleotides and phosphodiester bond-modified nucleotides are preferred as the nucleotide analog, and more specifically 2'-O-methylribose and a product with a phosphodiester bond substituted with a phosphorothioate bond are preferred. It is preferable that at least one nucleotide at each of the 3'- and 5'-ends of the sequence of the guide RNA be a nucleotide analog, and it is more preferable that at least two or three nucleotides at each of the 3'- and 5'-ends of the sequence of the guide RNA be each a nucleotide analog.

If the guide RNA is a chimeric RNA, it is preferable that at least one nucleotide at each of the 3'- and 5'-ends of the sequence of the guide RNA be a nucleotide analog; if the guide RNA is in the form of single RNAs that are not linked together (a combination of two RNAs) or two or more RNAs, it is preferable that at least one nucleotide at each of the 3'- and 5'-ends of the sequence of each RNA be a nucleotide analog (for example, it is preferable that each of the 3'- and 5'-ends of the crRNA and each of the 3'- and 5'-ends of the tracrRNA be a nucleotide analog).

If the guide RNA or the like and the RNA-guided nuclease or the like are to be in the form of a gene construct such as an expression plasmid, a sequence encoding the guide RNA and a sequence encoding the RNA-guided nuclease protein may be both included in one gene construct, and the sequences may be separately included in different gene constructs. As necessary, such a gene construct may include the sequence of any of a promoter, an enhancer, a start codon, a stop codon, a polyadenylation signal, a nuclear localization signal (NLS), a drug selection gene, and a reporter gene.

The composition of the present invention may be in any of (i) a mode in which only the guide RNA or the like (a guide RNA or a DNA including a sequence encoding the guide RNA) is included and the RNA-guided nuclease or the like (an RNA-guided nuclease or a nucleic acid including a sequence encoding the RNA-guided nuclease) is not included, (ii) a mode in which the guide RNA or the like is not included and only the RNA-guided nuclease or the like is included, and (iii) a mode in which both the guide RNA or the like and the RNA-guided nuclease or the like are included. If the guide RNA or the like is included, one type of a guide RNA may be included, and two types of guide RNAs or two or more types of guide RNAs may be included. In an embodiment of the composition of the present invention, it is preferable that the guide RNA be two types of guide RNAs or two or more types of guide RNAs.

In the present invention, only one component among multiple components required for CRISPR systems may be included in the lipid particle in the composition, and multiple components (e.g., a gRNA and an mRNA for Cas9) may be included in the lipid particle in the composition. If the lipid particle includes multiple components, for example, it is suitable to use an aqueous solution containing the components in appropriate concentrations (ratio) in production.

The composition of the present invention may contain multiple types of lipid particles each including one component. For example, a lipid particle including only a gRNA and a lipid particle including an mRNA for Cas9 may be mixed in the composition. If multiple types of lipid particles each including one component are mixed, it is suitable to set the concentrations (ratio) of the components to appropriate concentrations with considering gene modification efficiency and so on.

In a mode of the present invention, a lipid particle including the gRNA or the like and a lipid particle including the RNA-guided nuclease or the like in one composition (mixed solution) or in separate compositions are added to cells.

In a mode of the present invention, the composition of the present invention containing both the gRNA or the like and the RNA-guided nuclease or the like is added to cells.

The compound, lipid particle, and composition of the present invention can be stably used with low toxicity in a safe manner. In using the composition of the present invention in vivo, or using the composition as a drug, the composition is suitably administered to a subject (a human or a non-human mammal, preferably a human) so that an effective amount of the active ingredient in the composition of the present invention can be delivered to targeted cells.

In using the composition of the present invention ex vivo, or using the composition as a reagent, the composition of the present invention (in particular, the lipid particle contained therein and including the active ingredient) is suitably brought into contact with cells under culture, for example, by adding to the medium so that an effective amount of the active ingredient can migrate into cells.

The concentration of the active ingredient (the guide RNA or the like and the RNA-guided nuclease or the like) in the composition of the present invention may be appropriately controlled according to the purpose of the composition, and is not limited in any way. In using the composition of the present invention ex vivo, for example, the composition may be configured to allow such use that the composition of the present invention is stored as a composition containing a high concentration of the active ingredient, which is diluted with an appropriate solvent to prepare a composition with an appropriate concentration or added to a medium or the like. For example, a medium (culture solution) to which a lipid particle including the active ingredient of the present invention has been added is also a mode of the composition of the present invention, and the concentration of the active ingredient included in the lipid particle in the medium may be also appropriately controlled.

A method for producing the compound of the present invention is described below.

Raw materials and reagents used in each step of the production method below, and the obtained compound may each form a salt. Examples of such salts are the same as the above-mentioned salts for the compound of the present invention.

When a compound obtained in each step is a free compound, the compound may be converted into an intended salt by using a known method. Conversely, when a compound obtained in each step is a salt, the compound may be converted into a free form or another intended salt by using a known method.

A compound obtained in each step may be used for the subsequent reaction directly as a reaction solution, or a crude product may be obtained therefrom and used for the subsequent reaction. Alternatively, a compound obtained in each step may be isolated and/or purified from a reaction mixture according to a conventional method using a separation means such as concentration, crystallization, recrystallization, distillation, solvent extraction, fractional distillation, and chromatography.

If a compound as a raw material or reagent in each step is commercially available, the commercially available product may be directly used.

Reaction time for reaction in each step, which may vary depending on reagents and solvents to be used, is typically 1 minute to 48 hours, and preferably 10 minutes to 8 hours, unless otherwise specified.

Reaction temperature for reaction in each step, which may vary depending on reagents and solvents to be used, is typically −78° C. to 300° C., and preferably −78° C. to 150° C., unless otherwise specified.

Pressure for reaction in each step, which may vary depending on reagents and solvents to be used, is typically 1 atm to 20 atm, and preferably 1 atm to 3 atm, unless otherwise specified.

A microwave synthesis apparatus such as an Initiator produced by Biotage is occasionally used in reaction in a step. The reaction temperature, which may vary depending on reagents and solvents to be used, is typically room temperature to 300° C., preferably room temperature to 250° C., and more preferably 50° C. to 250° C., unless otherwise specified. The reaction time, which may vary depending on reagents and solvents to be used, is typically 1 minute to 48 hours, and preferably 1 minute to 8 hours, unless otherwise specified.

In reaction in each step, a reagent is used in an amount of 0.5 equivalents to 20 equivalents, preferably in an amount of 0.8 equivalents to 5 equivalents, to the amount of a substrate, unless otherwise specified. When a reagent is used as a catalyst, the reagent is used in an amount of 0.001 equivalents to 1 equivalent, preferably in an amount of 0.01 equivalents to 0.2 equivalents, to the amount of a substrate, unless otherwise specified. If a reagent serves as a reaction solvent in combination with its own role, the reagent is used in an amount as solvent.

In reaction in each step, the reaction is performed without solvent, or in an appropriate solvent dissolving or suspending reactants therein, unless otherwise stated. Examples of the solvent include solvents described in Examples and the following solvents.

Alcohols: methanol, ethanol, isopropanol, isobutanol, tert-butyl alcohol, 2-methoxyethanol, and so on;
ethers: diethyl ether, diisopropyl ether, diphenyl ether, tetrahydrofuran, 1,2-dimethoxyethane, and so on;
aromatic hydrocarbons: chlorobenzene, toluene, xylene, and so on;
saturated hydrocarbons: cyclohexane, hexane, heptane, and so on;
amides: N,N-dimethylformamide, N-methylpyrrolidone, and so on;
halogenated hydrocarbons: dichloromethane, carbon tetrachloride, and so on;
nitriles: acetonitrile and so on;
sulfoxides: dimethylsulfoxide and so on;
aromatic organic bases: pyridine and so on;
acid anhydride: acetic anhydride and so on;
organic acids: formic acid, acetic acid, trifluoroacetic acid, and so on;
inorganic acids: hydrochloric acid, sulfuric acid, and so on;
esters: ethyl acetate, isopropyl acetate, and so on;
ketones: acetone, methyl ethyl ketone, and so on; and water.

Two or more of these solvents may be mixed for use with an appropriate ratio.

When a base is used in reaction in each step, for example, any of bases listed below or bases described in Examples is used.

Inorganic bases: sodium hydroxide, potassium hydroxide, magnesium hydroxide, and so on;
basic salts: sodium carbonate, calcium carbonate, sodium hydrogen carbonate, and so on;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, and so on;
metal alkoxides: sodium ethoxide, potassium tert-butoxide, sodium tert-butoxide, and so on; alkali metal hydrides: sodium hydride and so on;
metal amides: sodium amide, lithium diisopropylamide, lithium hexamethyldisilazide, and so on; and
organolithiums: n-butyllithium, sec-butyllithium, and so on.

When an acid or an acidic catalyst is used in reaction in each step, for example, any of acids and acidic catalysts listed below and acids and acidic catalysts described in Examples is used.

Inorganic acids: hydrochloric acid, sulfuric acid, nitric acid, hydrobromic acid, phosphoric acid, and so on;
organic acids: acetic acid, trifluoroacetic acid, citric acid, p-toluenesulfonic acid, 10-camphorsulfonic acid, and so on; and
Lewis acids: boron trifluoride-diethyl ether complex, zinc iodide, anhydrous aluminum chloride, anhydrous zinc chloride, anhydrous iron chloride, and so on.

Unless otherwise specified, reaction in each step is performed in accordance with a known method such as a method described in The Fifth Series of Experimental Chemistry, Vol. 13 to 19 (The Chemical Society of Japan (ed.)); Shin Jikken Kagaku Koza (in Japanese, translated title: New Experimental Chemistry), Vol. 14 and 15 (The Chemical Society of Japan (ed.)); Seimitsu Yuki Kagaku (in Japanese, translated title: Precise Organic Chemistry, original title: Reaktionen und Synthesen im organisch-chemischen Praktikum und Forschungslaboratorium) Revised 2nd Edition (L. F. Tietze, Th. Eicher, Nankodo Co., Ltd.); Organic Name Reaction; The Reaction Mechanism and Essence Revised Edition (TOGO, Hideo, KODANSHA LTD.); ORGANIC SYNTHESES Collective Volume I to VII (John Wiley & Sons Inc.); Modern Organic Synthesis in the Laboratory A Collection of Standard Experimental Procedures (Jie Jack Li, Oxford University Pres); Comprehensive Heterocyclic Chemistry III, Vol. 1 to Vol. 14 (Elsevier Japan K.K.); Strategic Applications of Named Reactions in Organic Synthesis (translation supervisor: TOMIOKA, Kiyoshi, publisher: Kagaku-Dojin Publishing Company, INC.); Comprehensive Organic Transformations (VCH Publishers Inc.) (1989); or the like, or in accordance with a method described in Examples.

Protection or deprotection reaction for a functional group in each step is performed in accordance with a known method such as a method described in "Protective Groups in Organic Synthesis, 4th Ed." (Theodora W. Greene, Peter G. M. Wuts) published by Wiley-Interscience Publication, 2007; "Protecting Groups 3rd Ed." (P. J. Kocienski) published by Thieme Medical Publishers, 2004; or the like, or in accordance with a method described in Examples.

Examples of protective groups for a hydroxy group of alcohols or the like and phenolic hydroxy groups include ether-type protective groups such as methoxymethyl ether, benzyl ether, p-methoxybenzyl ether, t-butyldimethylsilyl ether, t-butyldiphenylsilyl ether, and tetrahydropyranyl ether; carboxylate-type protective groups such as acetate; sulfonate-type esters such as methanesulfonate; and carbonate-type protective groups such as t-butylcarbonate.

Examples of protective groups for a carbonyl group of aldehydes include acetal-type protective groups such as dimethylacetal; and cyclic acetal-type protective groups such as cyclic 1,3-dioxane.

Examples of protective groups for a carbonyl group of ketones include ketal-type protective groups such as dimethyl ketal; cyclic ketal-type protective groups such as cyclic 1,3-dioxane; oxime-type protective groups such as O-methyloxime; and hydrazone-type protective groups such as N,N-dimethylhydrazone.

Examples of protective groups for a carboxy group include ester-type protective groups such as methyl ester; and amide-type protective groups such as N,N-dimethylamide.

Examples of protective groups for thiol include ether-type protective groups such as benzyl thioether; and ester-type protective groups such as thioacetate, thiocarbonate, and thiocarbamate.

Examples of protective groups for an amino group and aromatic heterocycles such as imidazole, pyrrole, and indole include carbamate-type protective groups such as benzylcarbamate; amide-type protective groups such as acetamide; alkylamine-type protective groups such as N-triphenylmethylamine; and sulfonamide-type protective groups such as methanesulfonamide.

Removal of a protective group may be performed by using a known method such as a method using an acid, a base, ultraviolet light, hydrazine, phenylhydrazine, sodium N-methyldithiocarbamate, tetrabutylammonium fluoride, palladium acetate, or trialkylsilyl halide (e.g., trimethylsilyl iodide, trimethylsilyl bromide), or by using a reduction method.

Examples of reductants to be used when reduction reaction is performed in each step include metal hydrides such as lithium aluminium hydride, sodium triacetoxyborohydride, sodium cyanoborohydride, diisobutylaluminium hydride (DIBAL-H), sodium borohydride, and tetramethylammonium triacetoxyborohydride; boranes such as a borane-tetrahydrofuran complex; Raney nickel; Raney cobalt; hydrogen; and formic acid. For example, Raney nickel or Raney cobalt may be used in the presence of hydrogen or formic acid. When a carbon-carbon double bond or triple bond is reduced, a method using a catalyst such as palladium-carbon and Lindlar's catalyst may be used.

Examples of oxidants to be used when oxidation reaction is performed in each step include peracids such as m-chloroperbenzoic acid (MCPBA), hydrogen peroxide, and t-butylhydroperoxide; perchlorates such as tetrabutylammonium perchlorate; chlorates such as sodium chlorate; chlorites such as sodium chlorite; periodates such as sodium periodate; hypervalent iodine reagents such as iodosylbenzene; manganese-containing reagents such as manganese dioxide and potassium permanganate; leads such as lead tetraacetate; chromium-containing reagents such as pyridinium chlorochromate (PCC), pyridinium dichromate (PDC), and the Jones reagent; halogen compounds such as N-bromosuccinimide (NBS); oxygen; ozone; a sulfur trioxide-pyridine complex; osmium tetroxide; selenium dioxide; and 2,3-dichloro-5,6-dicyano-1,4-benzoquinone (DDQ).

Examples of radical initiators to be used when radical cyclization reaction is performed in each step include azo compounds such as azobisisobutyronitrile (AIBN); water-soluble radical initiators such as 4-4'-azobis-4-cyanopentanoic acid (ACPA); triethylboron in the presence of air or oxygen; and benzoyl peroxide. Examples of radical reaction reagents to be used include tributylstannane, tristrimethylsilylsilane, 1,1,2,2-tetraphenyldisilane, diphenylsilane, and samarium iodide.

Examples of Wittig reagents to be used when the Wittig reaction is performed in each step include alkylidenephosphoranes. Alkylidenephosphoranes may be prepared by using a known method such as reaction of a phosphonium salt and a strong base.

Examples of reagents to be used when the Horner-Emmons reaction is performed in each step include phosphonoacetates such as methyl dimethylphosphonoacetate and ethyl diethylphosphonoacetate; and bases such as alkali metal hydrides and organolithiums.

Examples of reagents to be used when the Friedel-Crafts reaction is performed in each step include a Lewis acid with an acid chloride or an alkylating agent (e.g., a halogenated alkyl, an alcohol, an olefin). Alternatively, an organic acid or an inorganic acid may be used instead of a Lewis acid, and an acid anhydride such as acetic anhydride may be used instead of an acid chloride.

When aromatic nucleophilic substitution reaction is performed in each step, a nucleophile (e.g., an amine, imidazole) and a base (e.g., a basic salt, an organic base) are used as reagents.

Examples of bases used to generate a carbanion when nucleophilic addition reaction with a carbanion, nucleophilic 1,4-addition reaction with a carbanion (Michael addition reaction), or nucleophilic substitution reaction with a carbanion is performed in each step include organolithiums, metal alkoxides, inorganic bases, and organic bases.

Examples of Grignard reagents to be used when the Grignard reaction is performed in each step include arylmagnesium halides such as phenylmagnesium bromide; and alkylmagnesium halides such as methylmagnesium bromide and isopropylmagnesium bromide. Grignard reagents may be prepared by using a known method such as reaction of a halogenated alkyl or halogenated aryl and metal magnesium in a solvent of an ether or tetrahydrofuran.

When the Knoevenagel condensation reaction is performed in each step, an active methylene compound sandwiched between two electron-withdrawing groups (e.g., malonic acid, diethyl malonate, malononitrile) and a base (e.g., an organic base, a metal alkoxide, an inorganic base) are used as reagents.

When the Vilsmeier-Haack reaction is performed in each is step, phosphoryl chloride and an amide derivative (e.g., N,N-dimethylformamide) are used as reagents.

Examples of azidating agents to be used when azidation reaction is performed for an alcohol, an alkyl halide, or a sulfonate in each step include diphenylphosphorylazide (DPPA), trimethylsilylazide, and sodium azide. When an alcohol is azidated, for example, a method using diphenylphosphorylazide and 1,8-diazabicyclo[5,4,0]undec-7-ene (DBU) or a method using trimethylsilylazide and a Lewis acid may be used.

Examples of reductants to be used when reductive amination reaction is performed in each step include sodium triacetoxyborohydride, sodium cyanoborohydride, hydrogen, and formic acid. Examples of carbonyl compounds to be used when the substrate is an amine compound include, in addition to paraformaldehyde, aldehydes such as acetaldehyde, and ketones such as cyclohexanone. Examples of amines to be used when the substrate is a carbonyl compound include ammonia; primary amines such as methyl amine; and secondary amines such as dimethylamine.

When the Mitsunobu reaction is performed in each step, an azodicarboxylate (e.g., diethyl azodicarboxylate (DEAD), diisopropyl azodicarboxylate (DIAD)) and triphenylphosphine are used as reagents.

Examples of reagents to be used when esterification reaction, amidation reaction, or urea formation reaction is performed in each step include halogenated acyl forms such as acid chlorides and acid bromides; and activated carboxylic acids such as acid anhydrides, activated ester forms, and sulfate forms. Examples of activators for carboxylic acids include carbodiimide condensing agents such as 1-ethyl-3-(3-dimethylaminopropyl)carbodiimide hydrochloride (WSCD); triazine-based condensing agents such as 4-(4,6-dimethoxy-1,3,5-triazin-2-yl)-4-methylmorpholinium chloride-n-hydrate (DMT-MM); carbonate condensing agents such as 1,1-carbonyldiimidazole (CDI); diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate; O-(7-azabenzotriazol-1-yl)-N,N,N',N'-tetramethyluronium hexafluorophosphate (HATU); sulfuric acid; and any combination of them. When a carbodiimide condensing agent is used, an additive such as 1-hydroxybenzotriazol is (HOBt), N-hydroxysuccinimide (HOSu), and dimethylaminopyridine (DMAP) may be further added to the reaction.

Examples of metal catalysts to be used when coupling reaction is performed in each step include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocenepalladium(II) chloride, and palladium(II) acetate; nickel compounds such as tetrakis(triphenylphosphine)nickel(0); rhodium compounds such as tris(triphenylphosphine)rhodium(III) chloride; cobalt compounds; copper compounds such as copper oxide and copper(I) iodide; and platinum compounds. A base may be further added to the reaction, and examples of the base include inorganic bases and basic salts.

When thiocarbonylation reaction is performed in each step, diphosphorus pentasulfide is typically used as a thiocarbonylating agent; however, not only diphosphorus pentasulfide, but also a reagent having 1,3,2,4-dithiadiphosphetane-2,4-disulfide structure such as 2,4-bis(4-methoxyphenyl)-1,3,2,4-dithiadiphosphetane-2,4-disulfide (Lowesson reagent) may be used.

Examples of halogenating agents to be used when the Wohl-Ziegler reaction is performed in each step include N-iodosuccinimide, N-bromosuccinimide (NBS), N-chlorosuccinimide (NCS), bromine, and sulfuryl chloride. The reaction may be further accelerated by addition of heat, light, or a radical initiator such as benzoyl peroxide and azobisisobutyronitrile.

Examples of halogenating agents to be used when halogenation reaction is performed for a hydroxy group in each step include hydrohalic acids and acid halides of inorganic acids, specifically, hydrochloric acid, thionyl chloride, phosphorus oxychloride for chlorination, and 48% hydrobromic acid for bromination. A method may be used in which a halogenated alkyl form is obtained from an alcohol by the action of triphenylphosphine and carbon tetrachloride, carbon tetrabromide, or the like. Alternatively, a method may be used in which a halogenated alkyl form is synthesized through two-step reaction such that an alcohol is converted into a sulfate and then reacted with lithium bromide, lithium chloride, or sodium iodide.

Examples of reagents to be used when the Arbuzov reaction is performed in each step include halogenated alkyls such as bromoethyl acetate; and phosphites such as triethylphosphite and tri(isopropyl)phosphite.

Examples of sulfonating agents to be used when sulfonation reaction is performed in each step include methanesulfonyl chloride, p-toluenesulfonyl chloride, methanesulfonic anhydride, p-toluenesulfonic anhydride, and trifluoromethanesulfonic anhydride.

When hydrolysis reaction is performed in each step, an acid or a base is used as a reagent. When acid hydrolysis reaction is performed for a t-butyl ester, formic acid or triethylsilane is added in some cases to reductively trap t-butyl cations produced as byproducts.

Examples of dehydrating agents to be used when dehydration reaction is performed in each step include sulfuric acid, diphosphorus pentoxide, phosphorus oxychloride, N,N'-dicyclohexylcarbodiimide, alumina, and polyphosphoric acid.

Compound (I) may be produced, for example, by using a production method shown below. Among the compounds (I), a compound in which each of the wavy lines forms a cis-type structure and a compound in which one or both of the wave lines forms a trans-type structure can be both produced by using the same production method as the production method shown below. In the present invention, compound (I) with a desired structure can be synthesized by using an appropriate raw material for the intended structure of compound (I) particularly in esterification. A salt of compound (I) can be obtained through appropriate mixing with an inorganic base, an organic base, an organic acid, or a basic or acidic amino acid.

[Formula 3]
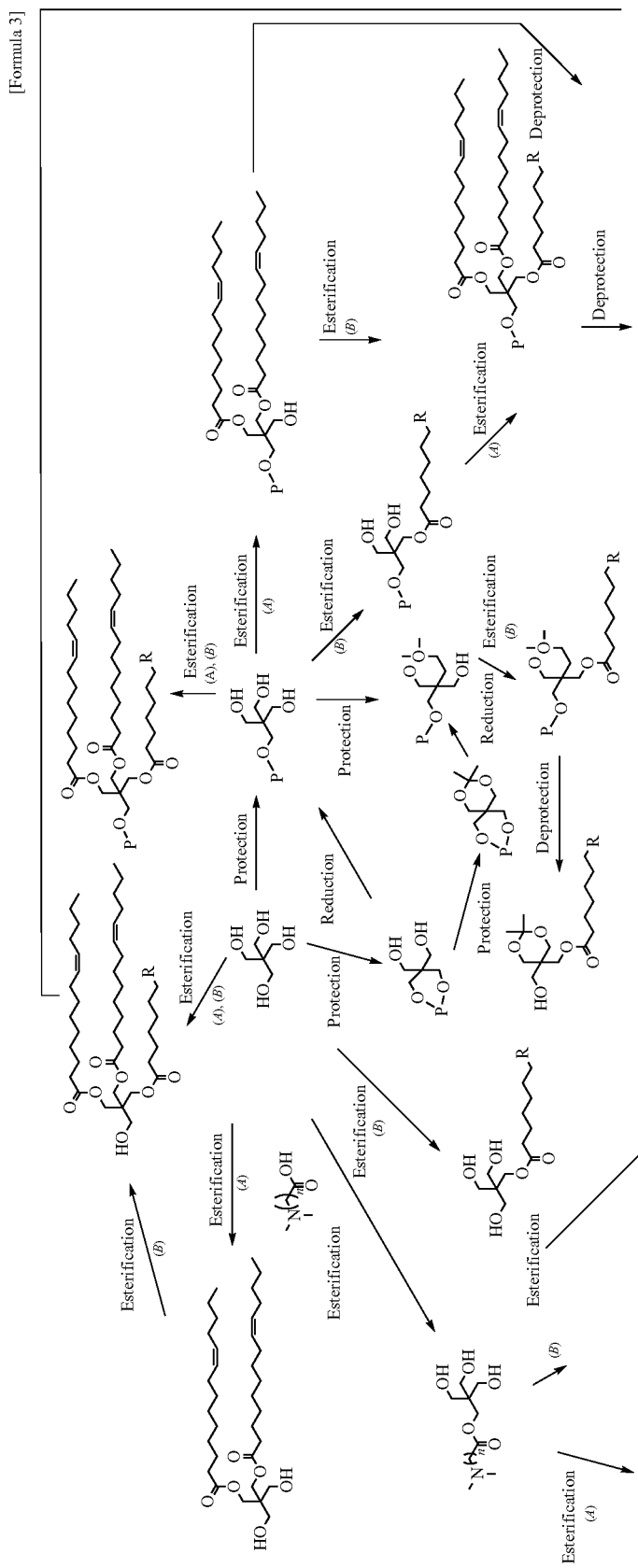

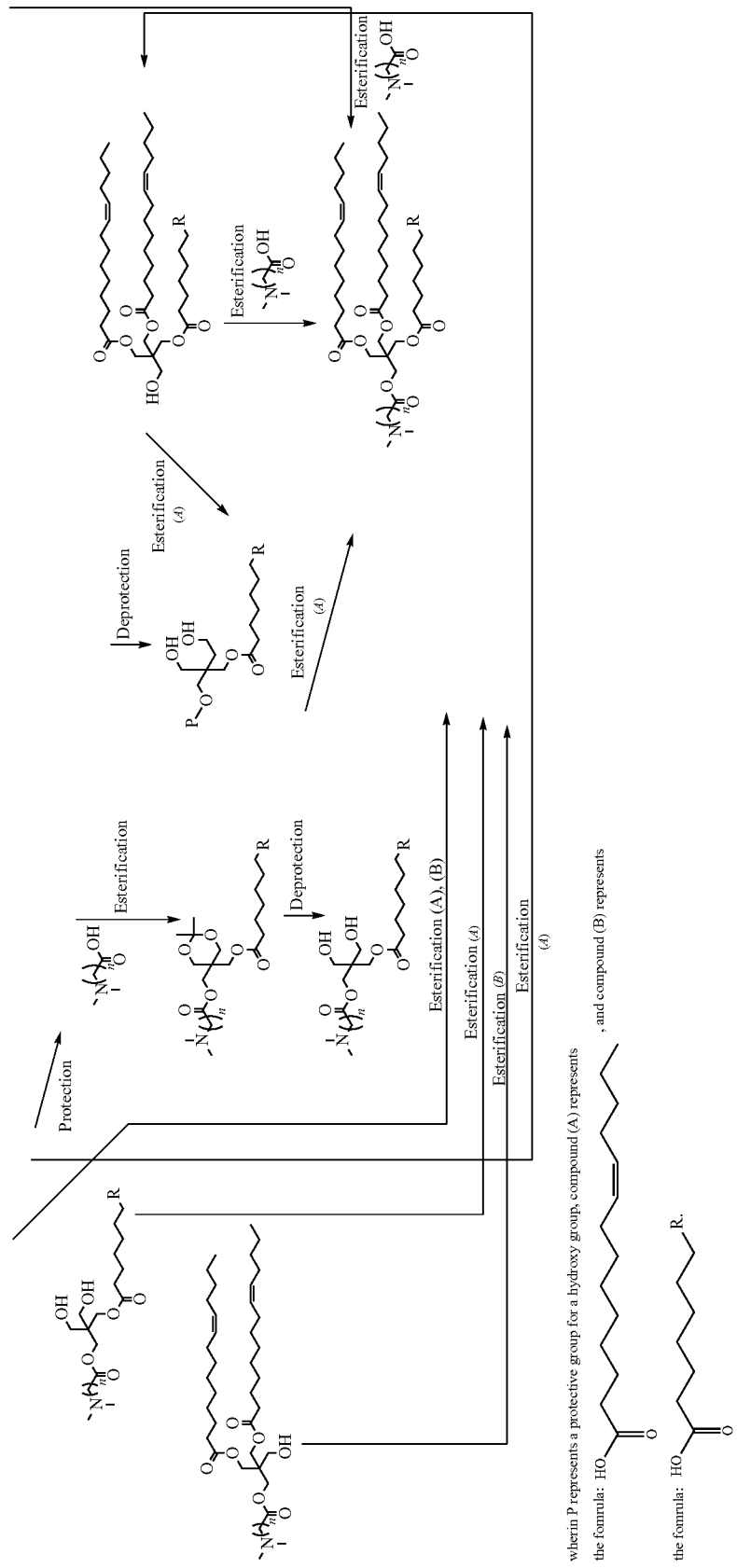

Now, a method for producing a lipid particle containing the compound of the present invention, and that for producing a composition containing the lipid particle, a guide RNA or a DNA including a sequence encoding the guide RNA, and/or an RNA-guided nuclease or a nucleic acid including a sequence encoding the RNA-guided nuclease will be described.

The lipid particle of the present invention can be produced by mixing the compound of the present invention (cationic lipid) and an additional lipid component, and then applying a known method to prepare a lipid particle from a lipid component. For example, the lipid particle can be produced as a lipid particle dispersion by dissolving the (mixed) lipid component in an organic solvent and mixing the obtained organic solvent solution with water or a buffer (e.g., through an emulsifying method). The mixing may be performed by using a microfluid mixing system (e.g., the apparatus NanoAssemblr (Precision NanoSystems). The lipid particle obtained may be subjected to desalting or dialysis and sterile filtration. As necessary, pH adjustment or osmotic pressure adjustment may be performed.

Compound (I) can form different structures depending on combination of the definitions of n, R, and the wavy lines of formula (I). To produce the lipid particle, one compound having a specific structure may be used alone as compound (I), and a mixture of a plurality of compounds of different structures may be used as compound (I).

Examples of the "additional lipid component" include the above-mentioned structural lipids such as sterols, phospholipids, and polyethylene glycol lipids. The "additional lipid component" is used, for example, in an amount of 0.008 to 4 mol per mole of the compound of the present invention. The compound of the present invention is preferably used as a mixture with the additional lipid component (in particular, cholesterol, phosphatidylcholine, and a polyethylene glycol lipid). In a preferred embodiment using a mixture of the compound of the present invention and the additional lipid component, the mixture is a mixture of 1 to 4 mol of the compound of the present invention, 0 to 3 mol of a sterol, 0 to 2 mol of a phospholipid, and 0 to 1 mol of a polyethylene glycol lipid. In a more preferred embodiment using a mixture of the compound of the present invention and the additional lipid component, the mixture is a mixture of 1 to 1.5 mol of the compound of the present invention, 0 to 1.25 mol of a sterol, 0 to 0.5 mol of a phospholipid, and 0 to 0.125 mol of a polyethylene glycol lipid.

The concentration of the compound of the present invention or the mixture of the compound of the present invention and the additional lipid component in the organic solvent solution is preferably 0.5 to 100 mg/mL.

Examples of the organic solvent include methanol, ethanol, 1-propanol, 2-propanol, 1-butanol, tert-butanol, acetone, acetonitrile, N,N-dimethylformamide, dimethylsulfoxide, and mixtures of them. The organic solvent may contain 0 to 20% of water or a buffer.

Examples of the buffer include acidic buffers (e.g., acetate buffer, citrate buffer, 2-morpholinoethanesulfonate (MES) buffer, phosphate buffer), and neutral buffers (e.g., 4-(2-hydroxyethyl)-1-piperazineethanesulfonate (HEPES) buffer, tris(hydroxymethyl)aminomethane (Tris) buffer, phosphate buffer, phosphate-buffered saline (PBS)).

If mixing is performed by using a microfluid mixing system, it is preferred to mix 1 to 5 parts by volume of water or the buffer per part by volume of the organic solvent solution. The flow rate of the mixed solution (mixed solution of the organic solvent solution and water or the buffer) in the system is preferably 0.1 to 10 mL/min, and the temperature is preferably 15 to 45° C.

The composition of the present invention can be produced as a lipid particle dispersion containing an active ingredient by adding in advance a nucleic acid (e.g., a guide RNA or a DNA including a sequence encoding the guide RNA, and/or an RNA-guided nuclease or a nucleic acid including a sequence encoding the RNA-guided nuclease) as an active ingredient to water or the buffer, as a result of which water or the buffer contains the nucleic acid, in production of the lipid particle or a lipid particle dispersion. The active ingredient is preferably added so that the active ingredient concentration of water or the buffer reaches 0.05 to 2.0 mg/mL. Herein, water or the buffer containing the active ingredient is occasionally referred to as "an aqueous solution containing the active ingredient (a guide RNA or a DNA including a sequence encoding the guide RNA, and/or an RNA-guided nuclease or a nucleic acid including a sequence encoding the RNA-guided nuclease)".

In producing the composition of the present invention containing two types or two or more types of guide RNAs as an active ingredient, it is preferred to use an aqueous solution containing two types or two or more types of guide RNAs in production of the composition.

In addition, the composition of the present invention can be produced as a lipid particle dispersion containing an active ingredient by admixing the lipid particle or a lipid particle dispersion and an active ingredient or an aqueous solution of the active ingredient through a known method. The lipid particle dispersion can be prepared by dispersing the lipid particle in an appropriate dispersion medium. The aqueous solution of the active ingredient can be prepared by dissolving the active ingredient in an appropriate solvent.

The content of the compound of the present invention in the composition of the present invention with the dispersion medium and solvent excluded is preferably 40 to 70% by weight.

The content of the active ingredient in the composition of the present invention with the dispersion medium and solvent excluded is preferably 1 to 20% by weight.

The dispersion medium of the lipid particle dispersion or the dispersion containing the composition can be replaced with water or a buffer through dialysis. The dialysis is performed with an ultrafiltration membrane having a molecular weight cutoff of 10 to 20K at 4° C. to room temperature. The dialysis may be repeatedly performed. For replacement of the dispersion medium, tangential flow filtration (TFF) may be used. After replacement of the dispersion medium, pH adjustment or osmotic pressure adjustment may be performed, as necessary.

Methods for analyzing a lipid particle containing the compound of the present invention, and a composition containing the lipid particle, and a guide RNA or a DNA including a sequence encoding the guide RNA, and/or an RNA-guided nuclease or a nucleic acid including a sequence encoding the RNA-guided nuclease are described below.

The particle size of the lipid particle (in the composition) can be measured by using a known means. For example, a Zetasizer Nano ZS (Malvern Instruments Limited), a particle size analyzer based on an NIBS (non-invasive backscatter) technique, can be used to calculate the particle size as a z-average particle size through cumulant analysis of the autocorrelation function. The particle size (average particle size) of the lipid particle (in the composition) is preferably 10 to 200 nm.

The concentration and encapsulation ratio of a nucleic acid (specifically, a guide RNA or a DNA including a sequence encoding the guide RNA, and/or an RNA-guided nuclease or a nucleic acid including a sequence encoding the RNA-guided nuclease) as an active ingredient in the composition of the present invention can be measured by using a known means. For example, after the nucleic acid is fluorescence-labeled with Quant-iT™ RiboGreen® (Invitrogen), the concentration and the inclusion ratio can be determined by measuring the fluorescence intensity. The concentration of the nucleic acid in the composition can be calculated by using a standard curve prepared from aqueous solutions of the nucleic acid with known concentrations, and the inclusion ratio can be calculated on the basis of difference in fluorescence intensity depending on the presence or absence of addition of Triton-X100 (a surfactant to disintegrate the lipid particle). The concentration in the composition refers to the total concentration of molecules of the nucleic acid included in the lipid particle and molecules of the nucleic acid not included in the lipid particle, and the inclusion ratio refers to the fraction of molecules of the nucleic acid included in the lipid particle to all the molecules of the nucleic acid in the composition.

Uses of the composition of the present invention are described below.

In a mode, the composition of the present invention may be used in a method for modifying a target gene locus in a cell, including a step of bringing the composition of the present invention into contact with a cell. A cell with a modified target gene locus can be obtained by using such a method.

In a mode, the composition of the present invention is may be used for producing a medicament containing the composition of the present invention. In other words, the composition of the present invention can be prepared as a medicament or formulated.

In a preferred mode of the present invention, the medicament is a prophylactic or therapeutic agent for dystrophinopathy (e.g., muscular dystrophy (Duchenne muscular dystrophy), dystrophin gene-associated dilated cardiomyopathy), or an agent for producing a repaired dystrophin protein. In other words, the composition of the present invention is, in a preferred mode of the present invention, used for a method for preventing or treating dystrophinopathy (e.g., muscular dystrophy (e.g., Duchenne muscular dystrophy, Becker's muscular dystrophy), dystrophin gene-associated dilated cardiomyopathy) (in particular, a method for preventing or treating Duchenne muscular dystrophy) in a mammal, or a method for producing repaired dystrophin protein, by administering an effective amount of the composition of the present invention.

Muscular dystrophy is defined as "a genetic disease that causes degeneration or necrosis of skeletal muscles as a major lesion and clinically presents as progressive muscle weakness". Known as muscular dystrophy are, for example, Duchenne muscular dystrophy, Becker's muscular dystrophy, Emery-Dreifuss muscular dystrophy, limb-girdle muscular dystrophy, congenital muscular dystrophy, Miyoshi muscular dystrophy, distal muscular dystrophy, facioscapulohumeral muscular dystrophy, and myotonic dystrophy.

Dystrophinopathy refers to various diseases caused by loss-of-function or dysfunctional dystrophin protein because of dystrophin gene mutation. Dystrophinopathy includes Duchenne muscular dystrophy, Becker's muscular dystrophy, and dystrophin gene-associated dilated cardiomyopathy. The main symptom is in most cases skeletal muscle disorder, but there exist cases without any skeletal muscle symptom. Some cases involve hyperCKemia, myoglobinuria, dilated cardiomyopathy, cognitive impairment, and so on.

Duchenne muscular dystrophy is a disease that is the most frequent among infantile muscular dystrophies, and the prevalence is 4 to 5 individuals per 100000 individuals. The main symptom is progressive muscle atrophy, and the cause is dysfunction of the dystrophin gene on the X-chromosome due to mutation. Half or more of patients with Duchenne muscular dystrophy have deletion of one or more exons. Dystrophin gene mutation offsets the reading frame for the protein to result in generation of an intervening stop codon, which leads to failed synthesis of dystrophin protein, thereby causing a series of symptoms.

The term "repaired dystrophin protein" herein refers to a dystrophin protein the expression of which has been recovered as a result of genome editing, in particular, a dystrophin protein that had a frameshift mutation or a nonsense mutation, but the expression of which has been recovered by using genome editing while an actin-binding domain at the N-terminus and a cysteine-rich domain at the C-terminus are retained. In the case that frameshift mutation occurs because of exon duplication, skipping one of the duplicated exons by genome editing can lead to recovery of expression to give a repaired dystrophin protein having 100% homology with healthy type. In particular, the term "repaired dystrophin protein" refers to a human dystrophin protein translated from an mRNA formed by skipping exon 45 and linking exon 43 and exon 46 together in a human dystrophin gene with exon 44 deleted. In addition to this, examples of repaired dystrophin proteins include, but are not limited to, a human dystrophin protein produced by skipping a specific exon in a human dystrophin gene with any of exons 12-44, 18-44, 46-47, 46-48, 46-49, 46-51, 46-53, and 46-55 deleted. Whether use of the composition of the present invention resulted in successful production of repaired dystrophin protein can be determined, for example, by detecting an mRNA encoding a repaired dystrophin protein in cells through PCR. Alternatively, determination can be made from the molecular weight of a dystrophin protein obtained by Western blotting with an antibody that recognizes the dystrophin protein.

In a mode, the composition of the present invention may be used in a method for producing a cell with a modified target gene locus, the method including the step of contacting the composition of the present invention with a cell.

In a mode, the composition of the present invention can be used in a method for producing a non-human mammal with a modified target gene locus, the method including the steps of: (1) bringing the composition of the present invention into contact with a fertilized ovum, embryonic stem cell, or oocyte of a non-human mammal; (2) selecting a fertilized ovum, embryonic stem cell, or oocyte with a modified target gene locus; and (3) transplanting the selected fertilized is ovum, embryonic stem cell, or oocyte into a female animal of a non-human mammal.

In step (1), the cells to be contacted with the composition of the present invention may be not only the above cells but also, for example, pluripotent stem cells such as iPS cells or germ cells such as spermatogonial stem cells and primordial germ cells.

The selection in step (2) may be performed by using a common screening method in CRISPR systems using a drug resistance gene, or by using PCR and sequence confirmation. For example, the selection may be in the following manner: a drug resistance gene expression unit is incorporated in advance in a vector for knock-in or knock-out; the drug resistance gene is expressed in a fertilized ovum or the like in which knock-in or knock-out was caused in a target gene locus by a CRISPR system; and the cell population is then subjected to drug treatment to select a fertilized ovum or the like with a modified target gene locus.

Details of the "composition" used in the modes relating to the above-described various methods, medicaments, and use of the present invention are as described above, and, for example, details and preferred modes of the guide RNA or the like and RNA-guided nuclease contained in the composition, the cell, and the target gene locus are also applied to the invention relating to a method and drug using the composition, and use of the composition.

The medicament of the present invention is preferably an injection, for example, for intravenous injection, intraarterial injection, intramuscular injection, subcutaneous injection, or intraperitoneal injection, but may be in a dosage form suitable for a different pathway as long as the dosage form can deliver an effective amount of the active ingredient to target cells even through the pathway. The injection is preferably for intravenous injection or intramuscular injection.

In addition to the composition of the present invention, the medicament of the present invention may contain a pharmaceutically acceptable substance, as necessary, such as water for injection, a solvent, and an excipient in preparing as an injection. The amount or concentration of the active ingredient in the medicament of the present invention may be appropriately adjusted in view of the dosage form, route of administration, dose per administration, frequency of administration in a given period, and so on so that an effective amount of the active ingredient for desired prophylactic or therapeutic effect can be delivered to target cells. The route of administration is preferably intravenous (systemic) administration or intramuscular administration.

"Treating" in the present invention refers to modifying a gene at a target gene locus in a certain fraction of cells in the living body (in a tissue or organ) of a subject who has already undergone the onset of a disease to repair the abnormality of the nucleotide sequence of a gene causing the disease. "Preventing" refers to modifying a gene at a target gene locus in a certain fraction of cells in the living body (in a tissue or organ) of a subject who has not undergone the onset of a disease or symptom to repair the nucleotide sequence of a gene that can cause the disease.

Examples of the abnormality of the nucleotide sequence of a gene causing the disease include gene mutation possibly involved in a disease (e.g., deletion of exon 44, which is found in some of patients with Duchenne muscular dystrophy). The composition of the present invention administered to a patient with Duchenne muscular dystrophy with deletion of exon 44, which causes failed production of dystrophin protein, induces production of repaired dystrophin protein (occasionally called recovery of dystrophin protein), and as a result the disease is successfully treated or prevented.

The fraction of cells with a modified gene (gene modification efficiency) in a tissue or organ and degrees of recovery or mitigation of symptoms of a disease, retardation or prevention of the onset, suppression of the progression, and so on are not specified in a limiting manner.

Examples of symptoms of muscular dystrophy include, but are not limited to, muscle weakness, muscular atrophy, deterioration of exercise capacity, gait disturbance, and myocardial disease. Treatment of muscular dystrophy includes amelioration of these symptoms and retardation of the onset or progression of them.

Therapeutic effect on muscular dystrophy can be evaluated by determining whether the onset, progression, or symptoms of muscular dystrophy are affected. More specifically, for example, therapeutic effect on muscular dystrophy can be confirmed by measuring muscle weight, muscle cross-sectional area, tension of an isolated skeletal muscle, muscle strength (e.g., grip strength), exercise capacity (e.g., treadmill capacity), and so on for a patient.

EXAMPLES

The present invention will be further described in detail with reference to Examples, Test Examples, and Formulation Examples; however, these do not limit the present invention, and modification may be made without departing from the scope of the present invention.

"Room temperature" in Examples below typically indicates approximately 10° C. to approximately 35° C. Each ratio shown for mixed solvent indicates a volume ratio, unless otherwise stated. % indicates % by weight, unless otherwise stated.

Elution in column chromatography was performed under observation with TLC (thin-layer chromatography), unless otherwise described. In TLC observation, a 60 $F_{254}$ produced by Merck KGaA was used as a TLC plate, and a solvent used as an elution solvent in column chromatography was used as an eluent. A UV detector was employed for detection, and observation was performed with a TLC coloring reagent, as necessary. In description of silica gel column chromatography, NH indicates that aminopropylsilane-bonded silica gel was used, and Diol indicates that 3-(2,3-dihydroxypropoxy)propylsilane-bonded silica gel was used. In description of preparative HPLC (high-performance liquid chromatography), C18 indicates that octadecyl-bonded silica gel was used. Each ratio shown for elution solvent indicates a volume ratio, unless otherwise stated.

$^1$H NMR was measured by using a Fourie transformation-NMR. The software ACD/SpecManager (product name) and so on were used for $^1$H NMR analysis. Description is occasionally omitted for peaks for a hydroxy group, an amino group, and so on with a very broad proton peak.

MS was measured through an LC/MS and an MALDI/TOFMS. For the ionization method, an ESI method, an APCI method, or an MALDI method was used. CHCA was used for the matrix. Measured values (found) were reported as data. In typical cases, some molecular ion peaks are observed as fragment ions. In the case of a salt, a molecular ion peak for the free form, or cationic, anionic, or fragment ion peaks are typically observed.

In Examples below, the following abbreviations are used.
MS: Mass spectrum
M: Molar concentration
N: Normality
$CDCl_3$: Deuterated chloroform
DMSO-$d_6$: Deuterated dimethylsulfoxide
$^1$H NMR: Proton nuclear magnetic resonance
LC/MS: Liquid chromatograph/mass spectrometer
ESI: Electrospray ionization
APCI: Atmospheric pressure chemical ionization
MALDI: Matrix-assisted laser desorption/ionization
TOFMS: Time-of-flight mass spectrometry
CHCA: α-Cyano-4-hydroxycinnamic acid
DMF: N,N-dimethylformamide
THF: Tetrahydrofuran
DMAP: 4-Dimethylaminopyridine
TBAF: Tetrabutylammonium fluoride

[Synthesis Example 1] 3-((4-(Dimethylamino)butanoyl)oxy)-2,2-bis(((9Z)-tetradec-9-enoyloxy)methyl)propyl (9Z)-tetradec-9-enoate A) 2-(((tert-Butyldimethylsilyl)oxy)methyl)-2-(hydroxymethyl)propane-1,3-diol To a mixture of 2,2-bis(hydroxymethyl)propane-1,3-diol (5.45 g), 1H-imidazole (2.72 g) and DMF (190 mL), a solution of tert-butylchlorodimethylsilane (3.01 g) in DMF (10 mL) was added at room temperature. After stirring for 24 hours, the reaction mixture was concentrated under reduced pressure. The residue was diluted with ethyl acetate, washed three times with water and once with brine, and then dried over anhydrous sodium sulfate, and the solvent was distilled off under reduced pressure. The residue was purified by silica gel column chromatography (ethyl acetate/hexane) to afford the title compound (2.25 g).

$^1$H NMR (300 MHz, CDCl$_3$) δ ppm 0.08 (6H, s), 0.90 (9H, s), 2.53 (3H, t, J=5.5 Hz), 3.66 (2H, s), 3.73 (6H, d, J=5.5 Hz)

B) 3-((tert-Butyl(dimethyl)silyl)oxy)-2,2-bis(((9Z)-tetradec-9-enoyloxy)methyl)propyl (9Z)-tetradec-9-enoate To a solution of 2-(((tert-butyldimethylsilyl)oxy)methyl)-2-(hydroxymethyl)propane-1,3-diol (258 mg), (9Z)-tetradec-9-enoic acid (769 mg) and DMAP (126 mg) in DMF (3 mL), 1-ethyl-3-(3-dimethylaminopropyl)carbodiimide hydrochloride (790 mg) was added at room temperature. After stirring for 18 hours, the reaction mixture was diluted with ethyl acetate, washed twice with water and once with brine, and then dried over anhydrous sodium sulfate, and the solvent was distilled off under reduced pressure. The residue was purified by silica gel column chromatography (NH, ethyl acetate/hexane) to afford the title compound (860 mg).

$^1$H NMR (300 MHz, CDCl$_3$) δ ppm 0.03 (6H, s), 0.81-0.96 (18H, m), 1.18-1.41 (36H, m), 1.53-1.67 (6H, m), 1.91-2.10 (12H, m), 2.29 (6H, t, J=7.6 Hz), 3.58 (2H, s), 4.08 (6H, s), 5.27-5.43 (6H, m)

C) 3-Hydroxy-2,2-bis(((9Z)-tetradec-9-enoyloxy)methyl)propyl (9Z)-tetradec-9-enoate To a solution of 3-((tert-butyl(dimethyl)silyl)oxy)-2,2-bis(((9Z)-tetradec-9-enoyloxy)methyl)propyl (9Z)-tetradec-9-enoate (5.91 g) in THF (120 mL), a mixture of a THF solution of TBAF (1 M, 14.85 mL) and acetic acid (4.91 mL) was added at room temperature. After stirring for 3 days, the reaction mixture was concentrated under reduced pressure. The residue was diluted with ethyl acetate, washed once with saturated aqueous solution of sodium hydrogen carbonate and once with brine, and then dried over anhydrous sodium sulfate, and the solvent was distilled off under reduced pressure. The residue was purified by silica gel column chromatography (ethyl acetate/hexane) to afford the title compound (4.96 g).

$^1$H NMR (300 MHz, CDCl$_3$) δ ppm 0.82-0.97 (9H, m), 1.16-1.42 (36H, m), 1.52-1.68 (6H, m), 1.90-2.12 (12H, m), 2.32 (6H, t, J=7.6 Hz), 2.52 (1H, t, J=7.0 Hz), 3.49 (2H, d, J=7.0 Hz), 4.11 (6H, s), 5.26-5.42 (6H, m)

D) 3-((4-(Dimethylamino)butanoyl)oxy)-2,2-bis(((9Z)-tetradec-9-enoyloxy)methyl)propyl (9Z)-tetradec-9-enoate To a solution of 3-hydroxy-2,2-bis(((9Z)-tetradec-9-enoyloxy)methyl)propyl (9Z)-tetradec-9-enoate (4.96 g), DMAP (796 mg) and 4-(dimethylamino)butanoic acid hydrochloride (2.19 g) in DMF (20 mL), 1-ethyl-3-(3-dimethylaminopropyl)carbodiimide hydrochloride (2.50 g) was added at room temperature. After stirring for 18 hours, the reaction mixture was diluted with ethyl acetate, washed once with saturated aqueous solution of sodium hydrogen carbonate and once with brine, and then dried over anhydrous sodium sulfate, and the solvent was distilled off under reduced pressure. The residue was purified by silica gel column chromatography (NH, ethyl acetate/hexane) to afford the title compound (5.31 g).

$^1$H NMR (300 MHz, CDCl$_3$) δ ppm 0.82-0.94 (9H, m), 1.20-1.42 (36H, m), 1.50-1.66 (6H, m), 1.69-1.83 (2H, m), 1.90-2.10 (12H, m), 2.20 (6H, s), 2.23-2.41 (10H, m), 4.11 (8H, s), 5.23-5.44 (6H, m)

The nucleotide sequences of MmRosa26 sgRNA (SEQ ID NO: 9) and two types of HsDMDEx45 sgRNAs (HsDMDEx45 #1 sgRNA and HsDMDEx45 #23 sgRNA, respectively corresponding to SEQ ID NOs: 1 and 2 shown above) used in Examples below are as follows.

TABLE 1

| ID | | sequence | |
|---|---|---|---|
| 1 | MmRosa26 sgRNA (mod) | G(M)^A(M)^U(M)^GGG CGGGAGUCUUCUGUUUUA GAGCUAGAAAUAGCAAGU UAAAAUAAGGCUAGUCCG UUAUCAACUUGAAAAAGU GGCACCGAGUCGGUGCU (M)^U(M)^U(M)^U | 98 mer RNA |
| 2 | HsDMD Ex45#1 sgRNA (mod) | U(M)^G(M)^G(M)^UAU CUUACAGGAACUCCGUUU UAGAGCUAGAAAUAGCAA GUUAAAAUAAGGCUAGUC CGUUAUCAACUUGAAAAA GUGGCACCGAGUCGG (M)^U(M)^G(M)^C | 96 mer RNA |
| 3 | HsDMD Ex45#23 sgRNA (mod) | A(M)^G(M)^C(M)^UGU CAGACAGAAAAAAGGUUU UAGAGCUAGAAAUAGCAA GUUAAAAUAAGGCUAGUC CGUUAUCAACUUGAAAAA GUGGCACCGAGUCGG (M)^U(M)^G(M)^C | 96 mer RNA |

N: RNA
N(M): 2'-OMe RNA
^: phosphorothioate

[Example 1] Evaluation of DNA Mutagenesis Efficiency in C57BL/6J Mice with MmRosa26 sgRNA

[1-1] Preparation of Cas9 mRNA-LNP

A lipid mixture (cationic lipid produced in Synthesis Example 1:DPPC:cholesterol:GM-020=60:10.6:28.7:0.7, in mole ratio) was dissolved in 90% EtOH/10% RNase-free water to afford a 6.9 mg/mL lipid solution. Cas9 mRNA (TriLink BioTechnologies) was dissolved in 10 mM 2-MES solution at pH 5.5 to afford a 0.15 mg/mL nucleic acid solution. The lipid solution and nucleic acid solution obtained were mixed by using a NanoAssemblr (Precision NanoSystems) at room temperature with a flow rate ratio of 2.7 mL/min:5.3 mL/min to afford a dispersion containing a lipid particle including the nucleic acid. By using a Slyde-A-Lyzer (molecular weight cutoff: 20 k, Thermo Fisher Scientific), the dispersion obtained was dialyzed with water at 4° C. for 1 hour and with PBS at 4° C. for 18 hours. Further, centrifugation (several times at 3,000×g and 4° C. for 20 minutes in each operation until the volume of the precipitate reached a constant volume) was performed with an Amicon (molecular weight cutoff: 30 k), and concentration was performed through ultrafiltration. Subsequently, filtration was performed with a 0.2 μm syringe filter (IWAKI CO., LTD.), and the resultant was stored at 4° C. The thus-prepared dispersion was used as "Cas9 mRNA-LNP" in a test described later. The particle size and polydispersity index (PDI) of the lipid particle were measured by using a Zetasizer Nano ZS (Malvern Instruments Limited). The nucleic acid concentration and inclusion ratio of the lipid particle were measured by using a Quant-iT™ RiboGreen® (Thermo Fisher Scientific). Table 2 shows the measurement results.

[1-2] Preparation of MmRosa26 sgRNA-LN

A lipid mixture (cationic lipid produced in Synthesis Example 1:DPPC:cholesterol:GM-020=60:10.6:28.7:0.7, in mole ratio) was dissolved in 90% EtOH/10% RNase-free water to afford a 6.9 mg/mL lipid solution. MmRosa26 sgRNA (GeneDesign Inc., see Table 1 shown above) was dissolved in 10 mM 2-MES solution at pH 5.5 to afford a 0.15 mg/mL nucleic acid solution. The lipid solution and nucleic acid solution obtained were mixed by using a NanoAssemblr (Precision NanoSystems) at room temperature with a flow rate ratio of 2.7 mL/min:5.3 mL/min to afford a dispersion containing a lipid particle including the nucleic acid. By using a Slyde-A-Lyzer (molecular weight cutoff: 20 k, Thermo Fisher Scientific), the dispersion obtained was dialyzed with water at 4° C. for 1 hour and with PBS at 4° C. for 18 hours. Further, centrifugation (several times at 3,000×g and 4° C. for 20 minutes in each operation until the volume of the precipitate reached a constant volume) was performed with an Amicon (molecular weight cutoff: 30 k), and concentration was performed through ultrafiltration. Subsequently, filtration was performed with a 0.2 μm syringe filter (IWAKI CO., LTD.), and the resultant was stored at 4° C. The thus-prepared dispersion was used as "MmRosa26 sgRNA-LNP" in a test described later. The particle size and polydispersity index (PDI) of the lipid particle were measured by using a Zetasizer Nano ZS (Malvern Instruments Limited). The nucleic acid concentration and inclusion ratio of the lipid particle were measured by using a Quant-iT™ RiboGreen® (Thermo Fisher Scientific). Table 2 shows the measurement results.

TABLE 2

|  | Nucleic acid concentration (μg/mL) | Inclusion ratio (%) | Particle size (nm) | PDI |
| --- | --- | --- | --- | --- |
| Cas9 mRNA-LNP | 950 | 96 | 82 | 0.028 |
| MmRosa sgRNA-LNP | 904 | 94 | 84.8 | 0.077 |

Figure 1:
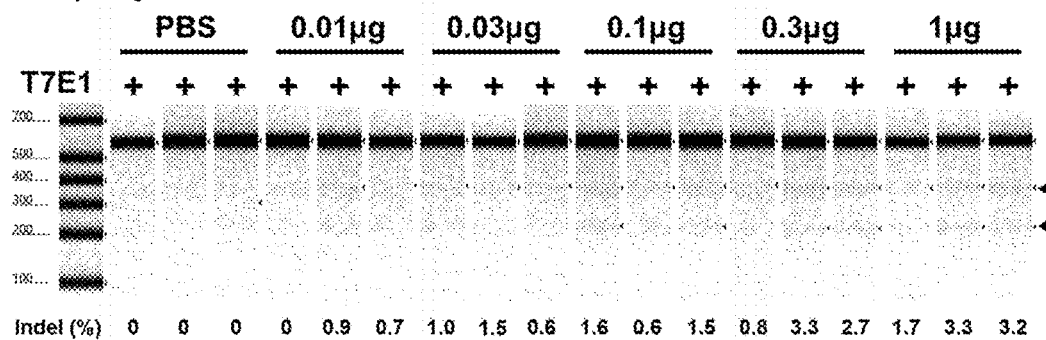
FIG. 1. shows the results of "Evaluation of DNA Mutagenesis Efficiency in C57BL/6J Mice with MmRosa26 sgRNA" in [1-3] of Example 1. [A]: Mutagenesis (indel) efficiencies calculated for different concentrations of sgRNA and Cas9 mRNA from an electropherogram and concentrations therein. [B]: A graph representing the relation between concentrations of sgRNA and Cas9 mRNA and mutagenesis efficiency, wherein the vertical axis represents mutagenesis (indel) efficiency (%) and the horizontal axis represents concentrations of sgRNA and Cas9 mRNA.
Figure 1:
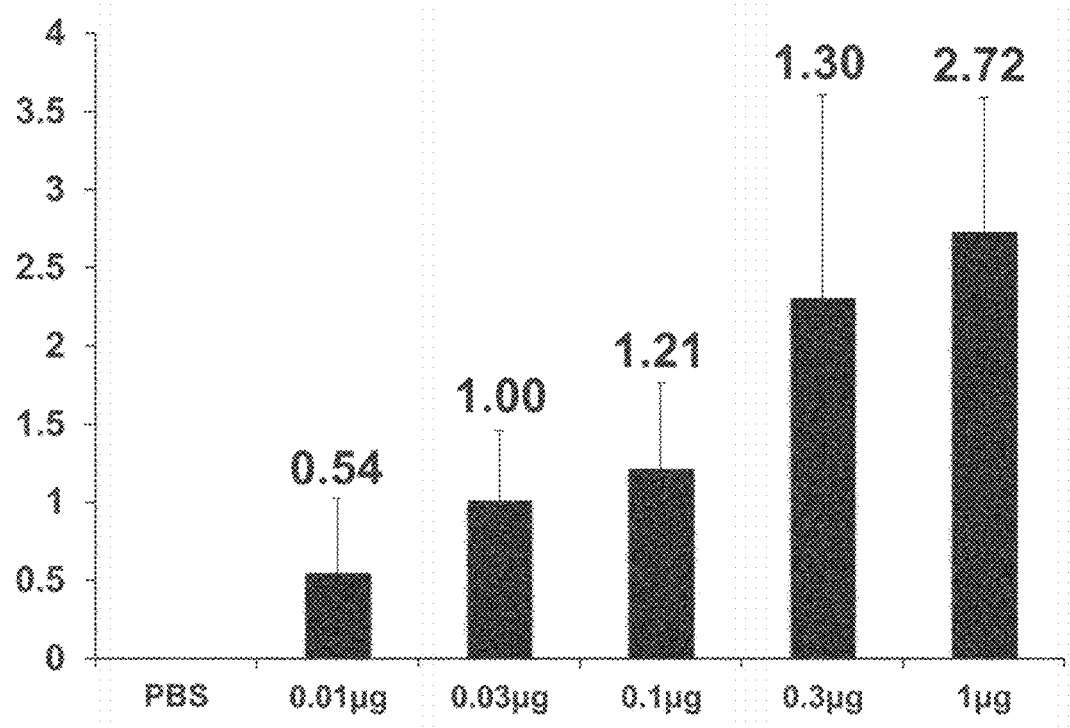

[1-3] Evaluation of DNA Mutagenesis Efficiency in C57BL/6J Mice with MmRosa26 sgRNA To the gastrocnemius muscle of the right lower limb of each 9-week-old male C57BL/6J mouse (CLEA Japan, Inc.), a mixed solution of MmRosa26 sgRNA-LNP and Cas9 mRNA-LNP (prepared by mixing the LNP dispersions so that the doses of sgRNA and mRNA each reached 0.01, 0.03, 0.1, 0.3, or 1 μg/mouse) or PBS was administered. Four days after the administration, the mice were euthanized by decapitation and bleeding under anesthesia with 3.5% isoflurane, and the skeletal muscle was then removed and quickly frozen with liquid nitrogen. From the frozen muscle tissue, the genomic DNA was extracted and purified by using a QIAamp Fast DNA Tissue Kit (QIAGEN), and PCR (Forward primer; SEQ ID NO: 10, Reverse primer; SEQ ID NO: 11) was performed by using PrimeSTAR GXL DNA polymerase (Takara Bio Inc.). The PCR product was purified by using a QIAquick PCR purification kit (QIAGEN), treated with T7 Endonuclease I (New England Biolabs Ltd.), and analyzed by using an Agilent 4200 TapeStation (Agilent Technologies). FIG. 1 shows the results.

SEQ ID NO: 10
5'-CTCCGAGGCGGATCACAAGCAATAATAACCTGTAG-3'

SEQ ID NO: 11
5'-TGCAAGCACGTTTCCGACTTGAGTTGCCTCAAGAG-3'

[Example 2] DNA Mutation Activity, Exon Skipping Effect, and Repaired Dystrophin Protein Expression Effect in Human DMD Exon 45-Knock-In/Mouse Dmd Exon 44-Knock-Out Mice

[2-1] Preparation of Cas9 mRNA-LNP

Cas9 mRNA-LNP was prepared again with the procedure described in [1-1] of Example 1, and the nucleic acid concentration, inclusion ratio, particle size, and PDI were measured. Table 3 shows the measurement results.

[2-2] Preparation of HsDMDEx45 #1 sgRNA-LNP

A lipid mixture (cationic lipid produced in Synthesis Example 1:DPPC:cholesterol:GM-020=60:10.6:28.7:0.7, in mole ratio) was dissolved in 90% EtOH/10% RNase-free water to afford a 6.9 mg/mL lipid solution. HsDMDEx45 #1 sgRNA (GeneDesign Inc., see Table 1 shown above) was dissolved in 10 mM 2-morpholinoethanesulfonic acid (MES) solution at pH 5.5 to afford a 0.15 mg/mL nucleic acid solution. The lipid solution and nucleic acid solution obtained were mixed by using a NanoAssemblr (Precision NanoSystems) at room temperature with a flow rate ratio of 2.7 mL/min:5.3 mL/min to afford a dispersion containing a lipid particle including the nucleic acid. By using a Slyde-A-Lyzer (molecular weight cutoff: 20 k, Thermo Fisher Scientific), the dispersion obtained was dialyzed with water at 4° C. for 1 hour and with PBS at 4° C. for 18 hours. Further, centrifugation (several times at 3,000×g and 4° C. for 20 minutes in each operation until the volume of the precipitate reached a constant volume) was performed with an Amicon (molecular weight is cutoff: 30 k), and concentration was performed through ultrafiltration. Subsequently, filtration was performed with a 0.2 μm syringe filter (IWAKI CO., LTD.), and the resultant was stored at 4° C. The thus-prepared dispersion was used as "HsDMDEx45 #1 sgRNA-LNP" in tests described later. The particle size and polydispersity index (PDI) of the lipid particle were measured by using a Zetasizer Nano ZS (Malvern Instruments Limited). The nucleic acid concentration and inclusion ratio of the lipid particle were measured by using a Quant-iT™ RiboGreen® (Thermo Fisher Scientific). Table 3 shows the measurement results.

TABLE 3

| | Nucleic acid concentration (μg/mL) | Inclusion ratio (%) | Particle size (nm) | PDI |
|---|---|---|---|---|
| Cas9 mRNA-LNP | 1102 | 94 | 83.1 | 0.091 |
| HsDMDEx45#1sgRNA-LNP | 1555 | 98 | 84.8 | 0.115 |

[2-3] Method for Producing Human DMD Exon 45-Knock-In/Mouse Dmd Exon 44-Knock-Out Mice Ten micrograms of a knock-in vector consisting of a sequence of 1.5 kb including human DMD exon 45 and 0.7 kb of the 5'-side of human DMD exon 45 and 0.6 kb of the 3'-side of human DMD exon 45, a neomycin-resistant gene expression unit sandwiched by FRT sequences, and sequences of 1.5 kb derived from mouse Dmd introns 44 and 45 was electroporated into $5×10^5$ C57BL/6J mouse-derived ES cells together with 2.5 μg of a pCAG-Cas9 expression vector and 2.5 μg of two types of pU6-sgRNA expression vectors (target sequences: SEQ ID NO: 12 and SEQ ID NO: 13), and a homologous recombinant cell line was selected through PCR and sequence confirmation. After the neomycin-resistant unit was removed through Flpe (flippase) treatment, the ES cell line was microinjected into a tetraploid blastocyst of an ICR mouse to obtain a chimeric mouse. A female human DMD exon 45-heteroknock-in mouse was obtained through in vitro fertilization between the chimeric mouse and a female C57BL/6J mouse. Subsequently, into each fertilized ovum obtained from a male C57BL/6J mouse and the female human DMD exon 45-heteroknock-in mouse, 100 ng/μL of Cas9 mRNA (TriLink BioTechnologies) and two types of sgRNAs for knock-out of mouse Dmd exon 44 (target sequences: SEQ ID NO: 14 and SEQ ID NO: 15, Fasmac Co., Ltd.) and 50 ng/μL of ssODN (SEQ ID NO: 16, Eurofins Genomics K.K.) were microinjected, and the obtained male babies were subjected to genetic determination through PCR and sequence confirmation to select human DMD exon 45-knock-in/mouse Dmd exon 44-knock-out mice.

```
                                        SEQ ID NO: 12
5'-atgaatgtgcctacatatgg-3'

SEQ ID NO: 13
5'-catagcatgcatttggcttc-3'

SEQ ID NO: 14
5'-gaatgaggtagtgttgtagg-3'

SEQ ID NO: 15
5'-gcaggaaatcatcttatagc-3'

SEQ ID NO: 16
5'-gagcaagctgggttagaacaaaggtctgtcagagtcagcatggga atgaggtagtgttgtagcaggaaatagtgtggtttaggtctctccccg ccctctgtgtatgtgtgtgtgtgtt-3'
```

[2-4] Evaluation of DNA Mutagenesis Efficiency in Skeletal Muscle

To the gastrocnemius muscle of the right lower limb of each 12-week-old male human DMD exon 45-knock-in/mouse Dmd exon 44-knock-out mouse, an LNP including 3 μg of HsDMD Ex45 #1 sgRNA and an LNP including 3 μg of SpCas9 mRNA (a mixed solution of Cas9 mRNA-LNP in [2-1] and HsDMDEx45 #1 sgRNA-LNP in [2-2]) was administered 6 times/2 weeks, and PBS was administered to the gastrocnemius muscle of the left lower limb 6 times/2 weeks. The mice were euthanized under anesthesia with 3.5% isoflurane 56 days after the first administration, and the skeletal muscle was then removed and quickly frozen with liquid nitrogen. The frozen muscle tissue was homogenized with RIPA buffer (Wako Pure Chemical Industries, Ltd.) containing 3% protenase inhibitor cocktail (Sgima) and 5 mM EDTA (Wako Pure Chemical Industries, Ltd.), and the genomic DNA was then extracted and purified by using a QIAamp Fast DNA Tissue Kit (QIAGEN), and amplified with PrimeSTAR GXL DNA polymerase (Takara Bio Inc.) and a primer set of SEQ ID NO: 17 (Forward primer) and SEQ ID NO: 18 (Reverse primer). The PCR product was purified by using a QIAquick PCR purification kit (QIAGEN), reannealed, and then treated with T7 Endonuclease I (New England Biolabs Ltd.), subjected to electrophoresis using an Agilent 4200 TapeStation (Agilent Technologies), and analyzed with the attached software. With the numerical values obtained, mutagenesis efficiency was calculated by using a calculation formula below (Expression 1).

```
                                        SEQ ID NO: 17
5'-CAAGTTTAAAATAGCAGAAAACCACTAACTAGCCA-3'

Figure 2:
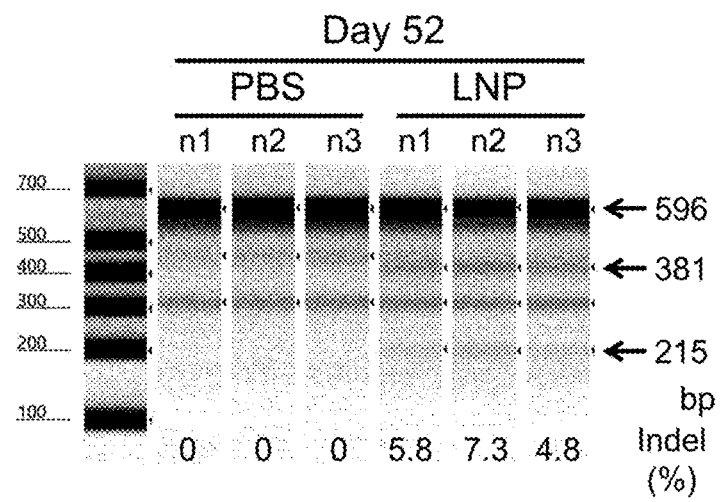
FIG. 2 shows the mutagenesis (indel) efficiencies calculated from an electropherogram and concentrations therein as results of "Evaluation of DNA Mutagenesis Efficiency in Skeletal Muscle" in [2-4] of Example 2.

SEQ ID NO: 18
5'-CTGACACATAAAAGGTGTCTTTCTGTCTTGTATCC-3'
```

$$f_{cut}=(b+c)/(a+b+c)$$

$$\text{ndel}(\%)=100×(1-\sqrt{(1-f_{cut})})\text{[Expression 1]}$$

a: Peak area of all bands b, c: Peak areas derived from bands cut into expected molecular weights The result found that, as shown in FIG. 2, specific DNA cleavage was detected from the skeletal muscle with administration of the LNPs in contrast to that with administration of PBS, and the mutagenesis efficiency was 5.84±2.15% (Mean±SD).

[2-5] Evaluation of Exon Skipping Efficiency in Skeletal Muscle

QIAzol Lysis Reagent (QIAGEN) and chloroform (Wako Pure Chemical Industries, Ltd.) were added to a part of the homogenate, and the resultant was mixed and centrifuged, and the water tank containing RNA was then separated and collected, and the total RNA was extracted and purified by using an RNeasy Mini Kit (QIAGEN). The total RNA was reverse-transcribed by using a High Capacity RNA-to-cDNA kit (Thermo Fisher Scientific), and subsequently amplified with PrimeSTAR GXL DNA polymerase (Takara Bio Inc.) and a primer set of SEQ ID NO: 19 (Forward primer) and SEQ ID NO: 20 (Reverse primer). The PCR product was purified by using a QIAquick PCR purification kit (QIAGEN), and then subjected to electrophoresis using an Agilent 4200 TapeStation (Agilent Technologies), and analyzed with the attached software. With the numerical values obtained, exon skipping efficiency was calculated by using a calculation formula below (Expression 2).

```
                                        SEQ ID NO: 19
5'-GGTGAAAGTACAGGAAGCCGT-3'

SEQ ID NO: 20
5'-TTAGCTGCTGCTCATCTCCAA-3'
``` exon skipping efficiency=100×b/(a+b)     [Expression 2]

a: Peak area of unskipped product band
b: Peak area of skipped product band

Figure 3:
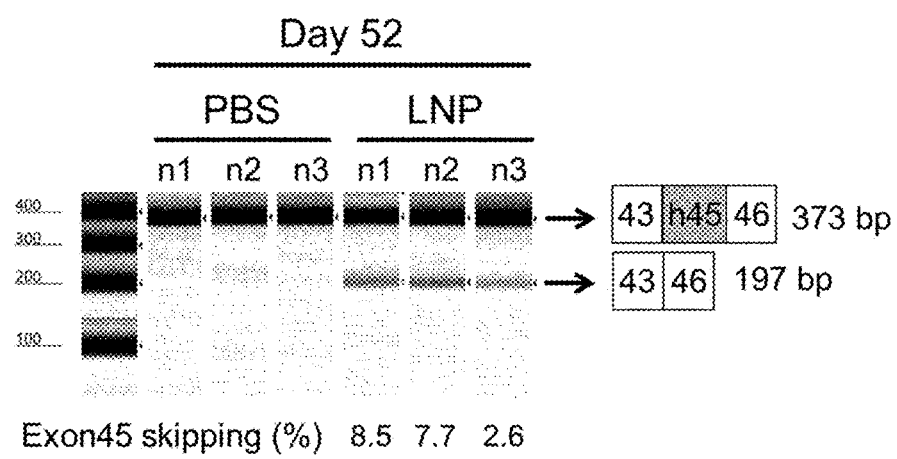
FIG. 3 shows the exon skipping efficiencies calculated from an electropherogram and concentrations therein as results of "Evaluation of Exon Skipping Efficiency in Skeletal Muscle" in [2-5] of Example 2.

The result found that, as shown in FIG. 3, a short PCR product with human Exon 45 skipped was detected from the skeletal muscle with administration of the LNPs in contrast to that with administration of PBS, and the efficiency was 5.07±2.59% (Mean±SD).

[2-6] Evaluation of Dystrophin Protein Recovery in Skeletal Muscle

A part of the homogenate was centrifuged, and the supernatant was recovered. The total protein in the supernatant was measured by using a Protein assay kit (Thermo Fisher Scientific) to adjust the total protein to 0.02 μg/uL and 3 μg/uL.

Detection of Gapdh: Sample buffer (Bio-Rad Laboratories, Inc.) containing a reductant (Thermo Fisher Scientific) was added to the supernatant adjusted to 0.02 μg/μL, and the resultant was treated at 98° C. for 10 minutes. To TGX ANY KD gel (Bio-Rad Laboratories, Inc.), 0.2 μg/10 μL of the reduced and heat-treated sample solution was added, and the resultant was subjected to electrophoresis at 200 V for 30 minutes. After the completion of the electrophoresis, the product was transferred onto a PVDF membrane by using a Trasblot turbo system (Bio-Rad Laboratories, Inc.). The PVDF membrane with the transferred product thereon was blocked with iBind Solution (Thermo Fisher Scientific) for 5 minutes, and subsequently blotted by using an iBind system (Themo) with an anti-GAPDH antibody (1:2000, Cell Signaling Technology, Inc.) and an HRP-labeled anti-rabbit IgG antibody (1:5000, GE Healthcare) each diluted with dilution buffer (TOYOBO CO., LTD.). The PVDF membrane after the completion of blotting was washed with distilled water, soaked in ECL Prime Western Blotting Detection Reagent (GE Healthcare) for approximately 5 minutes, and subjected to detection with ChemiDoc (Bio-Rad Laboratories, Inc.).

Detection of dystrophin: Sample buffer (Thermo Fisher Scientific) containing a reductant (Thermo Fisher Scientific) was added to the supernatant adjusted to 3 μg/μL, and the resultant was treated at 70° C. for 10 minutes. To 3-8% Tris-Acetate gel (Thermo Fisher Scientific), 30 μg/10 μL of the reduced and heat-treated sample solution was added, and the resultant was subjected to electrophoresis at 150 V for approximately 90 minutes. After the completion of the electrophoresis, the product was transferred onto a PVDF membrane by using a Trasblot turbo system (Bio-Rad Laboratories, Inc.). The PVDF membrane with the transferred product thereon was blocked with iBind Solution (Thermo Fisher Scientific) for 5 minutes, and subsequently blotted by using an iBind system (Thermo Fisher Scientific) with an anti-dystrophin antibody (1:2000, Abcam plc.) and an HRP-labeled anti-rabbit IgG antibody (1:5000, GE Healthcare) each diluted with dilution buffer (TOYOBO CO., LTD.). The PVDF membrane after the completion of blotting was washed with distilled water, soaked in ECL Select Western Blotting Detection Reagent (GE Healthcare) for approximately 5 minutes, and subjected to detection with Imager (Bio-Rad Laboratories, Inc.).

Gapdh and dystrophin detected with ChemiDoc were analyzed by using the software Image Lab (Bio-Rad Laboratories, Inc.), and relative expression levels were calculated as repaired dystrophin/Gapdh. FIG. 4 shows the results of the calculation. Significant expression of dystrophin was found for the group with administration of the LNPs in contrast to the group with administration of PBS.

[Example 3] DNA Mutagenesis Efficiency and Exon Skipping Efficiency in Human iPS Cell-Derived Myoblasts with HsDMDEx45 sgRNA (Part 1)

[3-1] Preparation of Cas9 mRNA-LNP

Cas9 mRNA-LNP was prepared again with the procedure described in [1-1] of Example 1, and the nucleic acid concentration, inclusion ratio, particle size, and PDI were measured. Table 4 shows the measurement results.

[3-2] Preparation of HsDMDEx45 #1 sgRNA-LNP

HsDMDEx45 #1 sgRNA-LNP produced in [2-2] of Example 2 was again used. The measurement results in Example 2 are shown again in Table 4.

TABLE 4

| | Nucleic acid concentration (μg/mL) | Inclusion ratio (%) | Particle size (nm) | PDI |
|---|---|---|---|---|
| Cas9 mRNA-LNP | 967 | 93 | 78.6 | 0.082 |
| HsDMDEx45#1 gRNA-LNP | 1555 | 98 | 84.8 | 0.115 |

[3-3] Myogenic Differentiation of Human iPS Cells and Introduction of LNPs

Human iPS cells derived from a patient with DMD with deletion of dystrophin Ex 45 and including a doxycycline-inducible MyoD expression cassette were suspended in an AK02N medium (Ajinomoto Co., Inc.) containing 10 μM Y-27632, and seeded on a 6-well plate coated with Matrigel at a density of 3×105 cells/well. The next day the medium was replaced with a Primate ES Cell Medium (ReproCELL Inc.), and the following day the medium was further replaced with a Primate ES Cell medium containing 1 μg/mL doxycycline to thereby initiate induction of MyoD gene expression. Twenty-four hours after the addition of doxycycline, the medium was replaced with an alpha Minimal Essential Medium (Sigma-Aldrich Co. LLC) containing 5% KSR and 1 μg/mL doxycycline, and culture was performed for 3 days. The medium was reduced to 700 μL, and a mixture of Cas9 mRNA-LNP (1, 3, or 10 g/well as mRNA) and HsDMDEx45 #1 sgRNA-LNP (1, 3, or 10 μg/well as sgRNA) was added thereto. Six hours after the addition, 1.3 mL of a medium (alpha Minimal Essential Medium, 5% KSR, 1 μg/mL doxycycline) was added.

Figure 5:
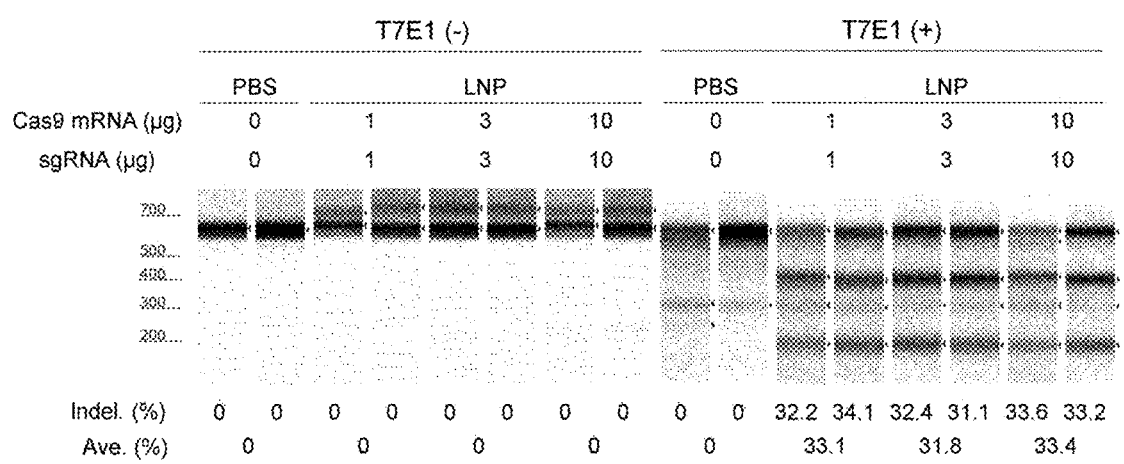
FIG. 5 shows the mutagenesis (indel) efficiencies calculated from an electropherogram and concentrations therein as results of "Evaluation of DNA Mutagenesis Efficiency in Human iPS Cell-Derived Myoblasts" in [3-4] of Example 3.

[3-4] Evaluation of DNA Mutagenesis Efficiency in Human iPS Cell-Derived Myoblasts Cells were collected 72 hours after the addition of the LNPs, and DNA was extracted and purified by using a QIAamp DNA mini kit (QIAGEN). A genomic region including the target sequence was amplified through PCR (Forward primer: SEQ ID NO: 17 shown above, Reverse primer: SEQ ID NO: 18 shown above) with PrimeSTAR GXL DNA polymerase (Takara Bio Inc.), and the PCR product obtained was purified by using a QIAquick PCR purification kit (QIAGEN). The purified DNA fragments were reannealed, then treated with T7 Endonuclease I (New England Biolabs Ltd.), subjected to electrophoresis using an Agilent 4200 TapeStation (Agilent Technologies), and analyzed with the attached software. The calculation formula for mutagenesis efficiency in [2-4] was applied (see Expression 1 shown above). FIG. 5 shows the results.

Figure 6:
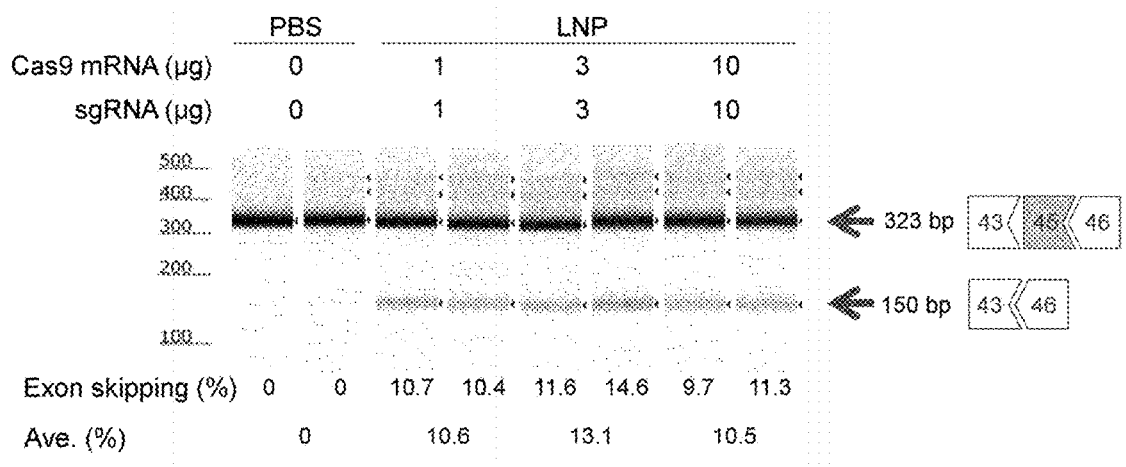
FIG. 6 shows the exon skipping efficiencies calculated from an electropherogram and concentrations therein as results of "Evaluation of Exon Skipping Efficiency in Human iPS Cell-Derived Myoblasts" in [3-5] of Example 3.

[3-5] Evaluation of Exon Skipping Efficiency in Human iPS Cell-Derived Myoblasts The total RNA was extracted and purified from the collected cells by using an RNA easy mini kit (QIAGEN). The total RNA was reverse-transcribed by using a High Capacity RNA-to-cDNA kit (Thermo Fisher Scientific), and subsequently PCR (Forward primer: SEQ ID NO: 21, Reverse primer: SEQ ID NO: 22) was performed with PrimeSTAR GXL DNA polymerase (Takara Bio Inc.). The PCR product obtained was purified by using a QIAquick PCR purification kit (QIAGEN), subjected to electrophoresis using an Agilent 4200 TapeStation, and analyzed with the attached software. The calculation formula for exon skipping efficiency in [2-5] was applied (see Expression 2 shown above). FIG. 6 shows the results.

SEQ ID NO: 21
5'-CTACAGGAAGCTCTCTCCCA-3'

SEQ ID NO: 22
5'-TGCTTCCTCCAACCATAAAACA-3'

[Example 4] Evaluation of Genome Editing Effect and is Exon Skipping Efficiency in Human iPS Cell-Derived Myoblasts with HsDMDEx45 sgRNA (Part 2)

[4-1] Preparation of Cas9 mRNA-LNP

Cas9 mRNA-LNP was prepared again with the procedure described in [1-1] of Example 1, and the nucleic acid concentration, inclusion ratio, particle size, and PDI were measured. Table 5 shows the measurement results.

[4-2] Preparation of HsDMDEx45 #1 sgRNA-LNP

HsDMDEx45 #1 sgRNA-LNP produced in [2-2] of Example 2 was again used. The measurement results in Example 2 are shown again in Table 5.

[4-3] Preparation of HsDMDEx45 #23 sgRNA-LNP

HsDMDEx45 #23 sgRNA-LNP was prepared with the same procedure as described in [2-2] of Example 2, except that "HsDmdEx45 #23 sgRNA" (see "HsDMDEx45 #23 sgRNA" in Table 1 shown above) was used in place of "HsDMDEx45 #1 sgRNA" (HsDMDEx45 #1 sgRNA in Example 4, see Table 1 shown above), and the nucleic acid concentration, inclusion ratio, particle size, and PDI were measured. Table 5 shows the measurement results.

TABLE 5

| | Nucleic acid concentration (μg/mL) | Inclusion ratio (%) | Particle size (nm) | PDI |
|---|---|---|---|---|
| Cas9 mRNA-LNP | 1040 | 96 | 78.2 | 0.085 |
| HsDMDEx45#1 sgRNA-LNP | 1587 | 98 | 83.8 | 0.081 |
| HsDMDEx45#23 sgRNA-LNP | 947 | 91 | 86.5 | 0.105 |

[4-4] Myogenic Differentiation of Human iPS Cells and Introduction of LNPs

Human iPS cells derived from a patient with DMD with deletion of dystrophin Ex 45 and including a doxycycline-inducible MyoD expression cassette, and human iPS cells derived from a healthy individual were each suspended in an AK02N medium (Ajinomoto Co., Inc.) containing 10 μM Y-27632, and seeded on a 6-well plate coated with Matrigel at a density of 1×105 cells/well. The next day the medium was replaced with a Primate ES Cell Medium (ReproCELL Inc.), and the following day the medium was further replaced with a medium (Primate ES Cell Medium) containing 1 μg/mL doxycycline to thereby initiate induction of MyoD gene expression. Twenty-four hours after the addition of doxycycline, the medium was replaced with an alpha Minimal Essential Medium (Sigma-Aldrich Co. LLC) containing 5% KSR is and 1 μg/mL doxycycline, and culture was performed for 3 days. The medium for patient-derived human iPS cells was reduced to 700 μL, and a mixture of LNPs was added thereto (see Table 6 below). Six hours after the addition, 1.3 mL of a medium (alpha Minimal Essential Medium, 5% KSR, 1 μg/mL doxycycline) was added.

TABLE 6

| sample | Cas9 mRNA-LNP (μg/well, as RNA) | HsDMDEx45#1 sgRNA-LNP (μg/well, as RNA) | HsDMDEx45#23 sgRNA-LNP (μg/well, as RNA) |
|---|---|---|---|
| PBS | 0 | 0 | 0 |
| Ex45#1 | 1 | 1 | 0 |
| Ex45#23 | 1 | 0 | 1 |
| Ex45#1 + Ex45#23 | 1 | 0.5 | 0.5 |

[4-5] Evaluation of Exon Skipping Efficiency in Human iPS Cell-Derived Myoblasts Each well was washed twice with cooled PBS 72 hours after the addition of LNPs, and cells were then collected with a Cell Scraper, and centrifuged at 4° C. and 15,000 rpm for 5 minutes. Thereafter, the supernatant was removed, and the cells were lysed with RIPA buffer. From a part of the cell lysate, the total RNA was extracted and purified by using an RNA easy mini kit (QIAGEN). The total RNA was reverse-transcribed by using a High Capacity RNA-to-cDNA kit (Thermo Fisher Scientific), and subsequently PCR (Forward primer: SEQ ID NO: 21 shown above, Reverse primer: SEQ ID NO: 22 shown above) was performed with PrimeSTAR GXL DNA polymerase (Takara Bio Inc.). The PCR product obtained was purified by using a QIAquick PCR purification kit (QIAGEN), subjected to electrophoresis using an Agilent 4200 TapeStation, and analyzed with the attached software.

Figure 7:
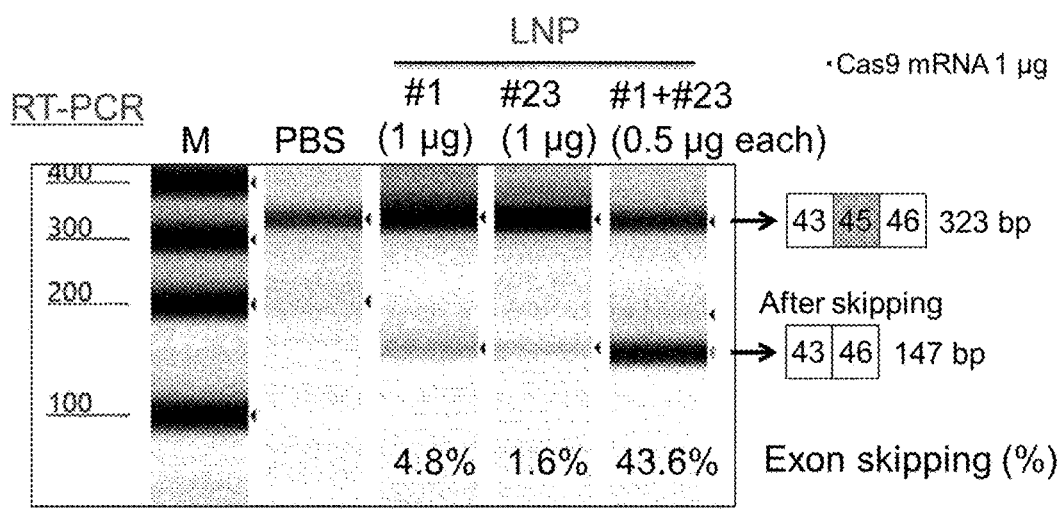
FIG. 7 shows exon skipping efficiencies calculated from an electropherogram and concentrations therein as results of "Evaluation of Exon Skipping Efficiency in Human iPS Cell-Derived Myoblasts" in [4-5] of Example 4.

The calculation formula for exon skipping efficiency in [2-5] was applied (see Expression 2 shown above). FIG. 7 shows the results.

[4-6] Evaluation of Dystrophin Protein Recovery in Human iPS Cell-Derived Myoblasts The total protein of a part of the cell lysate was measured by using a Protein assay kit (Thermo Fisher Scientific) to adjust the total protein to 0.083 μg/μL and 0.58 μg/μL.

Detection of Gapdh: Sample buffer (Bio-Rad Laboratories, Inc.) containing a reductant (Thermo Fisher Scientific) was added to the cell lysate adjusted to 0.083 μg/μL, and the resultant was treated at 98° C. for 10 minutes. To 10% Mini-PROTEAN TGX Precast Gel (Bio-Rad Laboratories, Inc.), 1 μg/12 μL of the reduced and heat-treated sample solution was added, and the resultant was subjected to electrophoresis at 150 V for 40 minutes. After the completion of the electrophoresis, the product was transferred onto a PVDF membrane by using a Trasblot turbo system (Bio-Rad Laboratories, Inc.). The PVDF membrane with the transferred product thereon was blocked with iBind Solution (Thermo Fisher Scientific) for 5 minutes, and subsequently blotted by using an iBind system (Themo) with an anti-GAPDH antibody (1:1000, Cell Signaling Technology, Inc.) and an HRP-labeled anti-rabbit IgG antibody (1:1000, GE Healthcare) each diluted with dilution buffer (TOYOBO CO., LTD.). The PVDF membrane after the completion of blotting was washed with distilled water, soaked in ECL Prime Western Blotting Detection Reagent (GE Healthcare) for approximately minutes, and subjected to detection with ChemiDoc (Bio-Rad Laboratories, Inc.).

Detection of dystrophin: Sample buffer (Thermo Fisher Scientific) containing a reductant (Thermo Fisher Scientific) was added to the supernatant adjusted to 0.58 μg/μL, and the resultant was treated at 70° C. for 10 minutes. To 3-8% Tris-Acetate gel (Thermo Fisher Scientific), 7 μg/12 μL of the reduced and heat-treated sample solution was added, and the resultant was subjected to electrophoresis at 150 V for approximately 90 minutes. After the completion of the electrophoresis, the product was transferred onto a PVDF membrane by using a Trasblot turbo system (Bio-Rad Laboratories, Inc.). The PVDF membrane with the transferred product thereon was blocked with iBind Solution (Thermo Fisher Scientific) for 5 minutes, and subsequently blotted by using an iBind system (Thermo Fisher Scientific) with an anti-dystrophin antibody (1:1000, Abcam plc.) and an HRP-labeled anti-rabbit IgG antibody (1:1000, GE Healthcare) each diluted with dilution buffer (TOYOBO CO., LTD.). The PVDF membrane after the completion of blotting was washed with distilled water, soaked in ECL Select Western Blotting Detection Reagent (GE) for approximately 5 minutes, and subjected to detection with ChemiDoc (Bio-Rad Laboratories, Inc.).

GAPDH and dystrophin detected with ChemiDoc were analyzed by using the software Image Lab (Bio-Rad Laboratories, Inc.), and the expression level of repaired dystrophin was corrected with respect to GAPDH to calculate the relative expression level of dystrophin to the expression level of dystrophin in human iPS cells derived from a healthy individual as 100%. FIG. 8 shows the results.

[Example 5] Evaluation of DNA Mutagenesis Efficiency in Different Tissues After Intravenous Administration of LNPs

[5-1] Preparation of Cas9 mRNA-LNP

A lipid mixture (cationic lipid produced in Synthesis Example 1:DPPC:cholesterol:GM-020=60:10.6:28.7:0.7, in mole ratio) was dissolved in 90% EtOH/10% RNase-free water to afford a 6.9 mg/mL lipid solution. Cas9 mRNA (TriLink BioTechnologies) was dissolved in 10 mM 2-MES solution at pH 5.5 to afford a 0.15 mg/mL nucleic acid solution. The lipid solution and nucleic acid solution obtained were mixed by using a NanoAssemblr (Precision NanoSystems) at room temperature with a flow rate ratio of 2.7 mL/min:5.3 mL/min to afford a dispersion containing a lipid particle including the nucleic acid. By using a Slyde-A-Lyzer (molecular weight cutoff: 20 k, Thermo Fisher Scientific), the dispersion obtained was dialyzed with water at 4° C. for 1 hour and with PBS at 4° C. for 18 hours. Further, centrifugation (several times at 3,000×g and 4° C. for 20 minutes in each operation until the volume of the precipitate reached a constant volume) was performed with an Amicon (molecular weight cutoff: 30 k), and concentration was performed through ultrafiltration. Subsequently, filtration was performed with a 0.2 μm syringe filter (IWAKI CO., LTD.), and the resultant was stored at 4° C. The thus-prepared dispersion was used as "Cas9 mRNA-LNP" in a test described later. The particle size and polydispersity index (PDI) of the lipid particle were measured by using a Zetasizer Nano ZS (Malvern Instruments Limited). The nucleic acid concentration and inclusion ratio of the lipid particle were measured by using a Quant-iT™ RiboGreen® (Thermo Fisher Scientific). Table 7 shows the results.

[5-2] Preparation of MmRosa26 sgRNA-LNP

A lipid mixture (cationic lipid produced in Synthesis Example 1:DPPC:cholesterol:GM-020=60:10.6:28.7:0.7, in mole ratio) was dissolved in 90% EtOH/10% RNase-free water to afford a 6.9 mg/mL lipid solution. MmRosa26 sgRNA (GeneDesign Inc., see Table 1 shown above) was dissolved in 10 mM 2-MES solution at pH 5.5 to afford a 0.15 mg/mL nucleic acid solution. The lipid solution and nucleic acid solution obtained were mixed by using a NanoAssemblr (Precision NanoSystems) at room temperature with a flow rate ratio of 2.7 mL/min:5.3 mL/min to afford a dispersion containing a lipid particle including the nucleic acid. By using a Slyde-A-Lyzer (molecular weight cutoff: 20 k, Thermo Fisher Scientific), the dispersion obtained was dialyzed with water at 4° C. for 1 hour and with PBS at 4° C. for 18 hours. Further, is centrifugation (several times at 3,000×g and 4° C. for 20 minutes in each operation until the volume of the precipitate reached a constant volume) was performed with an Amicon (molecular weight cutoff: 30 k), and concentration was performed through ultrafiltration. Subsequently, filtration was performed with a 0.2 μm syringe filter (IWAKI CO., LTD.), and the resultant was stored at 4° C. The thus-prepared dispersion was used as "MmRosa26 sgRNA-LNP" in a test described later. The particle size and polydispersity index (PDI) of the lipid particle were measured by using a Zetasizer Nano ZS (Malvern Instruments Limited). The nucleic acid concentration and inclusion ratio of the lipid particle were measured by using a Quant-iT™ RiboGreen® (Thermo Fisher Scientific). Table 7 shows the results.

TABLE 7

| | Nucleic acid concentration (μg/mL) | Inclusion ratio (%) | Particle size (nm) | PDI |
| --- | --- | --- | --- | --- |
| Cas9 mRNA-LNP | 1304 | 94 | 88.1 | 0.076 |
| MmRosa sgRNA-LNP | 1263 | 98 | 85.3 | 0.041 |

The LNP including 50 μg of mRosa26 sgRNA and that including 50 μg of pCas9 mRNA were administered to the tail vein of each 5-week-old male C57BL/6J mouse. After 7 days, the mice were euthanized by decapitation and bleeding under anesthesia with 3.5% isoflurane, and the gastrocnemius muscle, tibialis anterior muscle, quadriceps femoris muscle, diaphragm, and heart were then removed and quickly frozen with liquid nitrogen. The genomic DNA of each frozen tissue was extracted and purified by using a QIAamp Fast DNA Tissue Kit (QIAGEN), and amplified by using Q5 High-Fidelity DNA Polymerase (New England Biolabs Japan Inc.) and the following primer set (Forward primer: SEQ ID NO: 17 shown above, Reverse primer: SEQ ID NO: 18 shown above). The PCR product was purified by using a QIAquick 96 PCR BioRobot kit (QIAGEN), treated with T7 Endonuclease I (New England Biolabs Ltd.), subjected to electrophoresis using an Agilent 4200 TapeStation (Agilent Technologies), and analyzed with the attached software. With the numerical values obtained, mutagenesis efficiency was determined by using the above calculation formula (see Expression 1).

Figure 9:
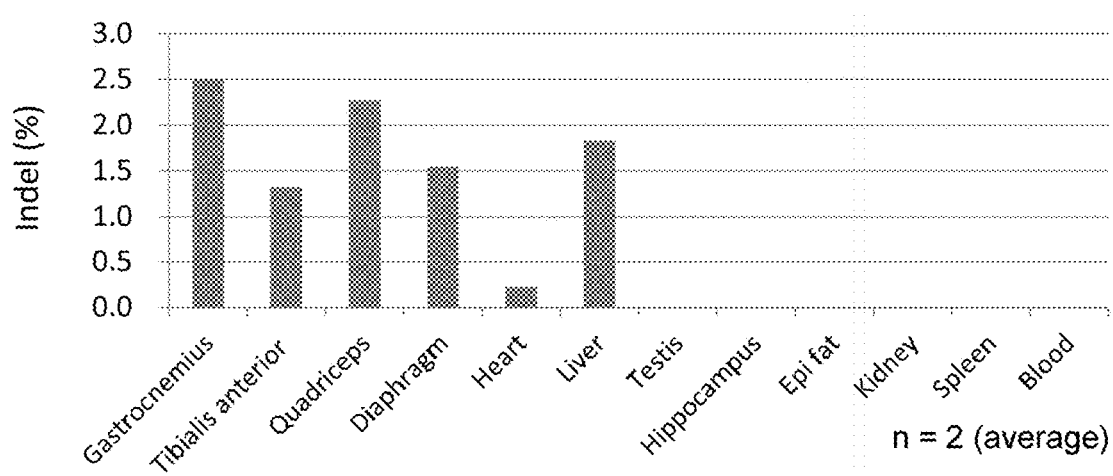
FIG. 9 shows the mutagenesis efficiencies as results of "Evaluation of DNA Cleavage Activity in Different Tissues After Intravenous Administration of LNPs" in Example 5.

The result found that, as shown in FIG. 9, mutagenesis in the target DNA was specifically detected in the skeletal muscles for the case with administration of the LNPs in contrast to the case with administration of PBS, and the displacement introduction efficiency was 2.50% for the gastrocnemius muscle, 1.32% for the tibialis anterior muscle, is 2.27% for the quadriceps femoris muscle, 1.54% for the diaphragm, 0.22% for the heart, and 1.83 for the liver. No mutagenesis was found in other tissues collected.

[Example 6] Evaluation of Exon Skipping Efficiency in Skeletal Muscle with Dual sgRNAs

[6-1] Preparation of Cas9 mRNA-LNP

A lipid mixture (cationic lipid produced in Synthesis Example 1:DPPC:cholesterol:GM-020=60:10.6:28.7:0.7, in mole ratio) was dissolved in 90% EtOH/10% RNase-free water to afford a 6.9 mg/mL lipid solution. Cas9 mRNA (TriLink BioTechnologies) was dissolved in 10 mM 2-MES solution at pH 5.5 to afford a 0.15 mg/mL nucleic acid solution. The lipid solution and nucleic acid solution obtained were mixed by using a NanoAssemblr (Precision NanoSystems) at room temperature with a flow rate ratio of 2.7 mL/min:5.3 mL/min to afford a dispersion containing a lipid particle including the nucleic acid. By using a Slyde-A-Lyzer (molecular weight cutoff: 20 k, Thermo Fisher Scientific), the dispersion obtained was dialyzed with water at 4° C. for 1 hour and with PBS at 4° C. for 18 hours. Further, centrifugation (several times at 3,000×g and 4° C. for 20 minutes in each operation until the volume of the precipitate reached a constant volume) was performed with an Amicon (molecular weight is cutoff: 30 k), and concentration was performed through ultrafiltration. Subsequently, filtration was performed with a 0.2 μm syringe filter (IWAKI CO., LTD.), and the resultant was stored at 4° C. The thus-prepared dispersion was used as "Cas9 mRNA-LNP" in a test described later. The particle size and polydispersity index (PDI) of the lipid particle were measured by using a Zetasizer Nano ZS (Malvern Instruments Limited). The nucleic acid concentration and inclusion ratio of the lipid particle were measured by using a Quant-iT™ RiboGreen® (Thermo Fisher Scientific). Table 8 shows the results.

[6-2] Preparation of HsDMDEx45 #1+#23 sgRNA-LNP

A lipid mixture (cationic lipid produced in Synthesis Example 1:DPPC:cholesterol:GM-020=60:10.6:28.7:0.7, in mole ratio) was dissolved in 90% EtOH/10% RNase-free water to afford a 6.9 mg/mL lipid solution. Equal amounts of HsDMDEx45 #1 sgRNA and HsDMDEx45 #23 sgRNA were dissolved in 10 mM 2-morpholinoethanesulfonic acid (MES) solution at pH 5.5 to afford a 0.15 mg/mL nucleic acid solution. The lipid solution and nucleic acid solution obtained were mixed by using a NanoAssemblr (Precision NanoSystems) at room temperature with a flow rate ratio of 2.7 mL/min:5.3 mL/min to afford a dispersion containing a lipid particle including the nucleic acids. By using a Slyde-A-Lyzer (molecular weight cutoff: 20 k, Thermo Fisher Scientific), the dispersion obtained was dialyzed with water at 4° C. for 1 hour and with PBS at 4° C. for 18 hours. Further, centrifugation (several times at 3,000×g and 4° C. for 20 minutes in each operation until the volume of the precipitate reached a constant volume) was performed with an Amicon (molecular weight cutoff: 30 k), and concentration was performed through ultrafiltration. Subsequently, filtration was performed with a 0.2 μm syringe filter (IWAKI CO., LTD.), and the resultant was stored at 4° C. The thus-prepared dispersion was used as "HsDMDEx45 #1+#23 sgRNA-LNP" in a test described later. The particle size and polydispersity index (PDI) of the lipid particle were measured by using a Zetasizer Nano ZS (Malvern Instruments Limited). The nucleic acid concentration and inclusion ratio of the lipid particle were measured by using a Quant-iT™ RiboGreen® (Thermo Fisher Scientific). Table 8 shows the results.

TABLE 8

|  | Nucleic acid concentration (μg/mL) | Inclusion ratio (%) | Particle size (nm) | PDI |
| --- | --- | --- | --- | --- |
| Cas9 mRNA-LNP | 1196 | 95 | 85.3 | 0.074 |
| HsDmdEx45 (#1 + 23) sgRNA-LNP | 785 | 94 | 85.9 | 0.091 |

To the gastrocnemius muscle of the right lower limb of each 6-week-old male human DMD exon 45-knock-in/mouse Dmd exon 44-knock-out mouse, the LNP including 3 μg of HsDMDEx45 #1+#23 and that including 3 μg of Cas9 mRNA were administered four times every other day. Fourteen days after the first administration, the mice were euthanized by decapitation and bleeding under anesthesia with 3.5% isoflurane, and the skeletal muscle was then removed and quickly frozen with liquid nitrogen. Qiazol (QIAGEN) was added to the frozen skeletal muscle to homogenize. Chloroform (Wako Pure Chemical Industries, Ltd.) was added thereto, and the resultant was mixed and centrifuged, and the water tank containing RNA was then separated and collected, and the total RNA was extracted and purified by using an RNeasy Mini Kit (QIAGEN). The total RNA was reverse-transcribed by using a High Capacity RNA-to-cDNA kit (Thermo Fisher Scientific), and subsequently amplified by using Q5 High-Fidelity DNA Polymerase (New England Biolabs Japan Inc.) and the following primer set (Forward primer: SEQ ID NO: 19 shown above, Reverse primer: SEQ ID NO: 20 shown above). The RT-PCR product was purified by using a QIAquick PCR purification kit (QIAGEN), and then subjected to electrophoresis using an Agilent 4200 TapeStation (Agilent Technologies), and analyzed with the attached software. With the numerical values obtained, exon skipping efficiency was determined by using the above calculation formula (see Expression 2).

Figure 10:
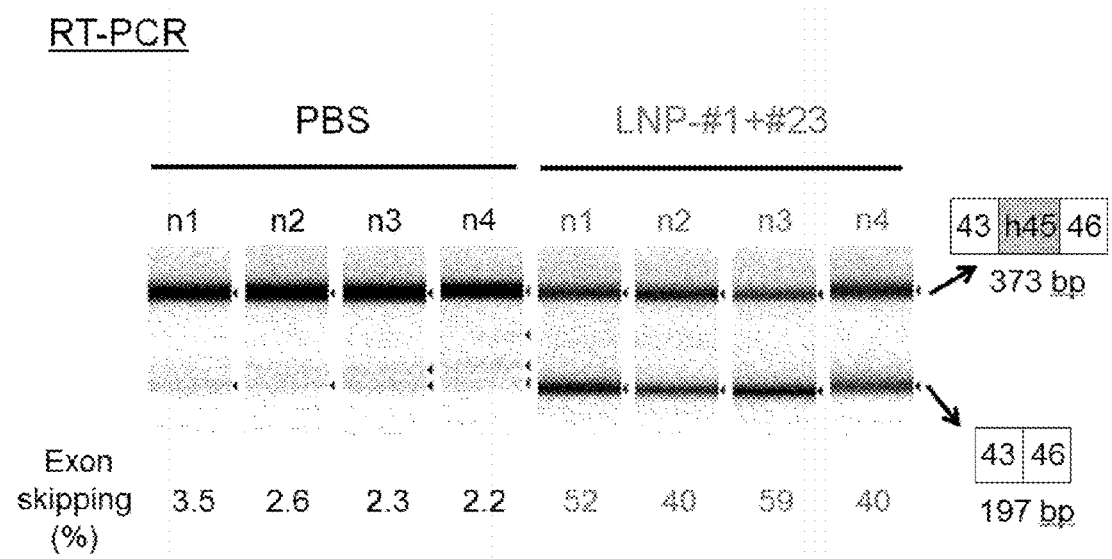
FIG. 10 shows the exon skipping efficiencies as results of "Evaluation of Exon Skipping Efficiency in Skeletal Muscle with Dual sgRNAs" in Example 6.

The result found that, as shown in FIG. 10, a short transcription product of the dystrophin gene with human Exon skipped was detected through RT-PCR from the skeletal muscle with administration of the LNPs in contrast to that with administration of PBS, and the exon skipping efficiency was 47.91±9.32% (Mean±SD) (PBS control: 2.63±0.62%).

INDUSTRIAL APPLICABILITY

The compound, lipid particle, and composition of the present invention enables efficient introduction of a gRNA or the like and an RNA-guided nuclease or the like used for CRISPR systems to various cells, tissues, and organs. Accordingly, the compound, lipid particle, and composition of the present invention are applicable as a DDS technique in CRISPR systems. In addition, the compound, lipid particle, and composition of the present invention are applicable as a prophylactic and/or therapeutic drug for various diseases is such as muscular dystrophy, or a reagent for research.

The invention claimed is:

1. A composition for inducing gene modification at a target gene locus in a cell, comprising:

1) A compound of formula (I):

(I)

[chemical structure]

wherein
   n represents an integer of 2 to 5,
   R represents a linear $C_{1-5}$ alkyl group, a linear $C_{7-11}$ alkenyl group, or a linear $C_{11}$ alkadienyl group, and
   wavy lines each independently represent a cis-type bond or a trans-type bond,
   or a salt thereof;

2) a structural lipid; and 3) a guide RNA or a DNA including a sequence encoding the guide RNA, and/or an RNA-guided nuclease or a nucleic acid including a sequence encoding the RNA-guided nuclease, wherein the guide RNA is a chimeric RNA.

2. The composition of claim 1, wherein the RNA-guided nuclease is Cas9.

3. The composition of claim 2, wherein the Cas9 is Cas9 derived from *Streptococcus pyogenes*.

4. The composition of claim 1, wherein the guide RNA is two or more types of guide RNAs.

5. The composition of claim 1, wherein the cell is a muscle cell.

6. The composition of claim 5, wherein the target gene locus includes a nucleotide sequence of a dystrophin gene.

7. The composition of claim 5, wherein the guide RNA is a chimeric RNA comprising the nucleic acid sequence of SEQ ID NO: 1 or SEQ ID NO: 2.

8. A method for modifying a target gene locus in a cell, comprising a step of contacting the composition of claim 1 with a cell.

9. The method of claim 8, wherein the RNA-guided nuclease is Cas9.

10. The method of claim 9, wherein the Cas9 is Cas9 derived from *Streptococcus pyogenes*.

11. The method of claim 8, wherein the cell is a muscle cell.

12. The method of claim 11, wherein the target gene locus includes a nucleotide sequence of a dystrophin gene.

13. The method of claim 11, wherein the guide RNA is a chimeric RNA comprising the nucleic acid sequence of SEQ ID NO: 1 or SEQ ID NO: 2.

14. A cell with a modified target gene locus, wherein the cell is obtained through the method of claim 8.

15. A medicament comprising the composition of claim 6.

16. The medicament of claim 15, wherein the RNA-guided nuclease is Cas9.

17. The medicament of claim 16, wherein the Cas9 is Cas9 derived from *Streptococcus pyogenes*.

18. The medicament of claim 15, wherein the guide RNA is a chimeric RNA comprising the nucleic acid sequence of SEQ ID NO: 1 or SEQ ID NO: 2.

19. The medicament of claim 15, which is an agent for prophylaxis or treatment of muscular dystrophy.

20. The medicament of claim 15, which is an agent for producing a repaired dystrophin protein.

21. The composition of claim 6 for use in preventing and/or treatment of muscular dystrophy.

22. A method for producing a cell with a modified target gene locus, comprising a step of bringing the composition of claim 1 into contact with a cell.

23. A method for producing a non-human mammal with a modified target gene locus, the method comprising the steps of:

(1) contacting the composition of claim 1 with a fertilized ovum, embryonic stem cell, or oocyte of a non-human mammal;
(2) selecting a fertilized ovum, embryonic stem cell, or oocyte with a modified target gene locus; and
(3) transplanting the selected fertilized ovum, embryonic stem cell, or oocyte into a female animal of a non-human mammal.

24. A method for producing a composition for inducing gene modification at a target gene locus in a cell, comprising a step of mixing a lipid particle dispersion and an aqueous solution together, wherein
the lipid particle dispersion comprises:
1) a compound of formula (I):

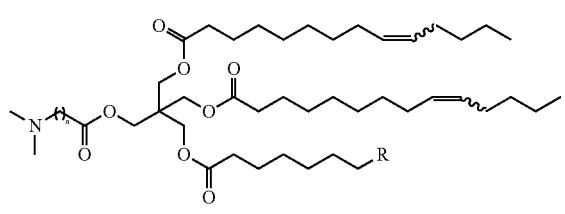

(I)

wherein
n represents an integer of 2 to 5,
R represents a linear $C_{1-5}$ alkyl group, a linear $C_{7-11}$ alkenyl group, or a linear $C_{11}$ alkadienyl group, and
wavy lines each independently represent a cis-type bond or a trans-type bond,
or a salt thereof; and
2) a structural lipid, and
the aqueous solution comprises:
3) a guide RNA or a DNA including a sequence encoding the guide RNA, and/or an RNA-guided nuclease or a nucleic acid including a sequence encoding the RNA-guided nuclease, wherein the guide RNA is a chimeric RNA.

25. The method of claim 24, wherein the guide RNA is two or more types of guide RNAs.

26. The composition of claim 1, wherein the compound is 3-((4-(dimethylamino)butanoyl)oxy)-2,2-bis(((9Z,9'Z)-tetradec-9-enoyloxy)methyl)propyl(9Z)-tetradec-9-enoate.

27. The method of claim 24, wherein the compound is 3-((4-(dimethylamino)butanoyl)oxy)-2,2-bis(((9Z,9'Z)-tetradec-9-enoyloxy)methyl)propyl(9Z)-tetradec-9-enoate.

\* \* \* \* \*

SEQUENCE LISTING

```
<160> NUMBER OF SEQ ID NOS: 22

<210> SEQ ID NO 1
<211> LENGTH: 96
<212> TYPE: RNA
<213> ORGANISM: Artificial Sequence
<220> FEATURE:
<223> OTHER INFORMATION: HsDMDEx45#1 sgRNA
<220> FEATURE:
<221> NAME/KEY: modified_base
<222> LOCATION: (1)..(1)
<223> OTHER INFORMATION: n stands for uracil (u) which may be 2'-O-
      methyluridine (um)
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: modified_base
<222> LOCATION: (2)..(2)
<223> OTHER INFORMATION: n stands for guanine (g) which may be 2'-O-
      methylguanosine (gm)
<220> FEATURE:
<221> NAME/KEY: modified_base
<222> LOCATION: (3)..(3)
<223> OTHER INFORMATION: n stands for guanine (g) which may be 2'-O-
      methylguanosine (gm)
<220> FEATURE:
<221> NAME/KEY: modified_base
<222> LOCATION: (93)..(93)
<223> OTHER INFORMATION: n stands for guanine (g) which may be 2'-O-
      methylguanosine (gm)
<220> FEATURE:
<221> NAME/KEY: misc_feature
<222> LOCATION: (93)..(95)
<223> OTHER INFORMATION: n is a, c, g, or u
<220> FEATURE:
<221> NAME/KEY: modified_base
<222> LOCATION: (94)..(94)
<223> OTHER INFORMATION: n stands for uracil (u) which may be 2'-O-
      methyluridine (um)
<220> FEATURE:
<221> NAME/KEY: modified_base
<222> LOCATION: (95)..(95)
<223> OTHER INFORMATION: n stands for guanine (g) which may be 2'-O-
      methylguanosine (gm)

<400> SEQUENCE: 1 nnnuacuua caggaacucc guuuuagagc uagaaauagc aaguuaaaau aaggcuaguc    60
cguuaucaac uugaaaaagu ggcaccgagu cgnnnc                             96

<210> SEQ ID NO 2
<211> LENGTH: 96
<212> TYPE: RNA
<213> ORGANISM: Artificial Sequence
<220> FEATURE:
<223> OTHER INFORMATION: HsDmdEx45#23 sgRNA
<220> FEATURE:
<221> NAME/KEY: modified_base
<222> LOCATION: (1)..(1)
<223> OTHER INFORMATION: n stands for adenine (a) which may be 2'-O-
      methyladenosine
```

```
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: modified_base
<222> LOCATION: (2)..(2)
<223> OTHER INFORMATION: n stands for guanine (g) which may be 2'-O-
      methylguanosine (gm)
<220> FEATURE:
<221> NAME/KEY: modified_base
<222> LOCATION: (3)..(3)
<223> OTHER INFORMATION: n stands for cytosine (c) which may be 2'-O-
      methylcytidine (cm)
<220> FEATURE:
<221> NAME/KEY: modified_base
<222> LOCATION: (93)..(93)
<223> OTHER INFORMATION: n stands for guanine (g) which may be 2'-O-
      methylguanosine (gm)
<220> FEATURE:
<221> NAME/KEY: misc_feature
<222> LOCATION: (93)..(95)
<223> OTHER INFORMATION: n is a, c, g, or u
<220> FEATURE:
<221> NAME/KEY: modified_base
<222> LOCATION: (94)..(94)
<223> OTHER INFORMATION: n stands for uracil (u) which may be 2'-O-
      methyluridine (um)
<220> FEATURE:
<221> NAME/KEY: modified_base
<222> LOCATION: (95)..(95)
<223> OTHER INFORMATION: n stands for guanine (g) which may be 2'-O-
      methylguanosine (gm)

<400> SEQUENCE: 2
nnnugucaga cagaaaaaag guuuuagagc uagaaauagc aaguuaaaau aaggcuaguc     60
cguuaucaac uugaaaaagu ggcaccgagu cgnnnc                              96

<210> SEQ ID NO 3
<211> LENGTH: 20
<212> TYPE: RNA
<213> ORGANISM: Artificial Sequence
<220> FEATURE:
<223> OTHER INFORMATION: Target-recognizing sequence of HsDmdEX#1 sgRNA
<220> FEATURE:
<221> NAME/KEY: modified_base
<222> LOCATION: (1)..(1)
<223> OTHER INFORMATION: n stands for uracil (u) which may be 2'-O-
      methyluridine (um)
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: modified_base
<222> LOCATION: (2)..(2)
<223> OTHER INFORMATION: n stands for guanine (g) which may be 2'-O-
      methylguanosine (gm)
<220> FEATURE:
<221> NAME/KEY: modified_base
<222> LOCATION: (3)..(3)
<223> OTHER INFORMATION: n stands for guanine (g) which may be 2'-O-
      methylguanosine (gm)

<400> SEQUENCE: 3
nnnuaucuua caggaacucc                                                20

<210> SEQ ID NO 4
<211> LENGTH: 20
<212> TYPE: RNA
<213> ORGANISM: Artificial Sequence
<220> FEATURE:
<223> OTHER INFORMATION: Target-recognizing sequence of HsDmdEX#23 sgRNA
<220> FEATURE:
```

```
<221> NAME/KEY: modified_base
<222> LOCATION: (1)..(1)
<223> OTHER INFORMATION: n stands for adenine (a) which may be 2'-O-
      methyladenosine
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: modified_base
<222> LOCATION: (2)..(2)
<223> OTHER INFORMATION: n stands for guanine (g) which may be 2'-O-
      methylguanosine (gm)
<220> FEATURE:
<221> NAME/KEY: modified_base
<222> LOCATION: (3)..(3)
<223> OTHER INFORMATION: n stands for cytosine (c) which may be 2'-O-
      methylcytidine (cm)

<400> SEQUENCE: 4
nnnugucaga cagaaaaaag                                                    20

<210> SEQ ID NO 5
<211> LENGTH: 32
<212> TYPE: RNA
<213> ORGANISM: Artificial Sequence
<220> FEATURE:
<223> OTHER INFORMATION: crRNA sequence of HsDmdEX#1 sgRNA
<220> FEATURE:
<221> NAME/KEY: modified_base
<222> LOCATION: (1)..(1)
<223> OTHER INFORMATION: n stands for uracil (u) which may be 2'-O-
      methyluridine (um)
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: modified_base
<222> LOCATION: (2)..(2)
<223> OTHER INFORMATION: n stands for guanine (g) which may be 2'-O-
      methylguanosine (gm)
<220> FEATURE:
<221> NAME/KEY: modified_base
<222> LOCATION: (3)..(3)
<223> OTHER INFORMATION: n stands for guanine (g) which may be 2'-O-
      methylguanosine (gm)

<400> SEQUENCE: 5
nnnuaucuua caggaacucc guuuuagagc ua                                      32

<210> SEQ ID NO 6
<211> LENGTH: 32
<212> TYPE: RNA
<213> ORGANISM: Artificial Sequence
<220> FEATURE:
<223> OTHER INFORMATION: crRNA sequence of HsDmdEX#23 sgRNA
<220> FEATURE:
<221> NAME/KEY: modified_base
<222> LOCATION: (1)..(1)
<223> OTHER INFORMATION: n stands for adenine (a) which may be 2'-O-
      methyladenosine
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: modified_base
<222> LOCATION: (2)..(2)
<223> OTHER INFORMATION: n stands for guanine (g) which may be 2'-O-
      methylguanosine (gm)
<220> FEATURE:
<221> NAME/KEY: modified_base
<222> LOCATION: (3)..(3)
<223> OTHER INFORMATION: n stands for cytosine (c) which may be 2'-O-
```

-continued methylcytidine (cm)

<400> SEQUENCE: 6
nnnugucaga cagaaaaaag guuuuagagc ua                                      32

<210> SEQ ID NO 7
<211> LENGTH: 60
<212> TYPE: RNA
<213> ORGANISM: Artificial Sequence
<220> FEATURE:
<223> OTHER INFORMATION: tracrRNA sequence of HsDmdEX#1 sgRNA
<220> FEATURE:
<221> NAME/KEY: modified_base
<222> LOCATION: (57)..(57)
<223> OTHER INFORMATION: n stands for guanine (g) which may be 2'-O-
      methylguanosine (gm)
<220> FEATURE:
<221> NAME/KEY: misc_feature
<222> LOCATION: (57)..(59)
<223> OTHER INFORMATION: n is a, c, g, or u
<220> FEATURE:
<221> NAME/KEY: modified_base
<222> LOCATION: (58)..(58)
<223> OTHER INFORMATION: n stands for uracil (u) which may be 2'-O-
      methyluridine (um)
<220> FEATURE:
<221> NAME/KEY: modified_base
<222> LOCATION: (59)..(59)
<223> OTHER INFORMATION: n stands for guanine (g) which may be 2'-O-
      methylguanosine (gm)

<400> SEQUENCE: 7
uagcaaguua aauuaaggcu aguccguuau caacuugaaa aaguggcacc gagucgnnnc         60

<210> SEQ ID NO 8
<211> LENGTH: 60
<212> TYPE: RNA
<213> ORGANISM: Artificial Sequence
<220> FEATURE:
<223> OTHER INFORMATION: tracrRNA sequence of HsDmdEX#23 sgRNA
<220> FEATURE:
<221> NAME/KEY: modified_base
<222> LOCATION: (57)..(57)
<223> OTHER INFORMATION: n stands for guanine (g) which may be 2'-O-
      methylguanosine (gm)
<220> FEATURE:
<221> NAME/KEY: misc_feature
<222> LOCATION: (57)..(59)
<223> OTHER INFORMATION: n is a, c, g, or u
<220> FEATURE:
<221> NAME/KEY: modified_base
<222> LOCATION: (58)..(58)
<223> OTHER INFORMATION: n stands for uracil (u) which may be 2'-O-
      methyluridine (um)
<220> FEATURE:
<221> NAME/KEY: modified_base
<222> LOCATION: (59)..(59)
<223> OTHER INFORMATION: n stands for guanine (g) which may be 2'-O-
      methylguanosine (gm)

<400> SEQUENCE: 8
uagcaaguua aauuaaggcu aguccguuau caacuugaaa aaguggcacc gagucgnnnc         60

<210> SEQ ID NO 9
<211> LENGTH: 98
<212> TYPE: RNA
<213> ORGANISM: Artificial Sequence
<220> FEATURE:
<223> OTHER INFORMATION: MmRosa26 sgRNA
<220> FEATURE:
<221> NAME/KEY: modified_base
<222> LOCATION: (1)..(1)
<223> OTHER INFORMATION: gm

```
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (95)..(95)
<223> OTHER INFORMATION: um
<220> FEATURE:
<221> NAME/KEY: misc_feature
<222> LOCATION: (95)..(97)
<223> OTHER INFORMATION: n is a, c, g, or u
<220> FEATURE:
<221> NAME/KEY: modified_base
<222> LOCATION: (96)..(96)
<223> OTHER INFORMATION: um
<220> FEATURE:
<221> NAME/KEY: modified_base
<222> LOCATION: (97)..(97)
<223> OTHER INFORMATION: um

<400> SEQUENCE: 9
nnngggcggg agucuucugu uuuagagcua gaaauagcaa guuaaaauaa ggcuaguccg      60
uuaucaacuu gaaaagugg caccgagucg gugcnnnu                              98

<210> SEQ ID NO 10
<211> LENGTH: 35
<212> TYPE: DNA
<213> ORGANISM: Artificial Sequence
<220> FEATURE:
<223> OTHER INFORMATION: Forward primer used in Example 1[1-3]

<400> SEQUENCE: 10
ctccgaggcg gatcacaagc aataataacc tgtag                                35

<210> SEQ ID NO 11
<211> LENGTH: 35
<212> TYPE: DNA
<213> ORGANISM: Artificial Sequence
<220> FEATURE:
<223> OTHER INFORMATION: Reverse primer used in Example 1[1-3]

<400> SEQUENCE: 11
tgcaagcacg tttccgactt gagttgcctc aagag                                35

<210> SEQ ID NO 12
<211> LENGTH: 20
<212> TYPE: DNA
<213> ORGANISM: Mus musculus

<400> SEQUENCE: 12
atgaatgtgc ctacatatgg                                                 20

<210> SEQ ID NO 13
<211> LENGTH: 20
<212> TYPE: DNA
<213> ORGANISM: Mus musculus

<400> SEQUENCE: 13
catagcatgc atttggcttc                                                 20

<210> SEQ ID NO 14
<211> LENGTH: 20
<212> TYPE: DNA
```

<213> ORGANISM: Mus musculus

<400> SEQUENCE: 14
gaatgaggta gtgttgtagg                                                 20

<210> SEQ ID NO 15
<211> LENGTH: 20
<212> TYPE: DNA
<213> ORGANISM: Mus musculus

<400> SEQUENCE: 15
gcaggaaatc atcttatagc                                                 20

<210> SEQ ID NO 16
<211> LENGTH: 120
<212> TYPE: DNA
<213> ORGANISM: Artificial Sequence
<220> FEATURE:
<223> OTHER INFORMATION: ssODN used in Example 2[2-3]

<400> SEQUENCE: 16
gagcaagctg ggttagaaca aaggtctgtc agagtcagca tgggaatgag gtagtgttgt      60
agcaggaaat agtgtggttt aggtctctcc ccgccctctg tgtatgtgtg tgtgtgtgtt     120

<210> SEQ ID NO 17
<211> LENGTH: 35
<212> TYPE: DNA
<213> ORGANISM: Artificial Sequence
<220> FEATURE:
<223> OTHER INFORMATION: Forward primer used in Example 2[2-4] and
      [2-5], and Example 5

<400> SEQUENCE: 17
caagtttaaa atagcagaaa accactaact agcca                                35

<210> SEQ ID NO 18
<211> LENGTH: 35
<212> TYPE: DNA
<213> ORGANISM: Artificial Sequence
<220> FEATURE:
<223> OTHER INFORMATION: Reverse primer used in Example 2[2-4] and
      [2-5], and Example 5

<400> SEQUENCE: 18
ctgacacata aaggtgtct ttctgtcttg tatcc                                 35

<210> SEQ ID NO 19
<211> LENGTH: 21
<212> TYPE: DNA
<213> ORGANISM: Artificial Sequence
<220> FEATURE:
<223> OTHER INFORMATION: Forward primer used in Example 2[2-5] and
      Example 6

<400> SEQUENCE: 19
ggtgaaagta caggaagccg t                                               21

<210> SEQ ID NO 20
<211> LENGTH: 21
<212> TYPE: DNA
<213> ORGANISM: Artificial Sequence
<220> FEATURE:
<223> OTHER INFORMATION: Reverse primer used in Example 2[2-5] and
      Example 6

<400> SEQUENCE: 20

```
ttagctgctg ctcatctcca a                                              21

<210> SEQ ID NO 21
<211> LENGTH: 20
<212> TYPE: DNA
<213> ORGANISM: Artificial Sequence
<220> FEATURE:
<223> OTHER INFORMATION: Forward primer used in Example 3[3-5] and
      Example 4[4-5]

<400> SEQUENCE: 21
ctacaggaag ctctctccca                                                20

<210> SEQ ID NO 22
<211> LENGTH: 22
<212> TYPE: DNA
<213> ORGANISM: Artificial Sequence
<220> FEATURE:
<223> OTHER INFORMATION: Reverse primer used in Example 3[3-5] and
      Example 4[4-5]

<400> SEQUENCE: 22
tgcttcctcc aaccataaaa ca                                             22
```